(12) United States Patent
Allison

US006982154B2

(10) Patent No.: US 6,982,154 B2
(45) Date of Patent: Jan. 3, 2006

(54) MODIFIED ANNEXIN PROTEINS AND METHODS FOR TREATING VASO-OCCLUSIVE SICKLE-CELL DISEASE

(75) Inventor: Anthony Allison, Belmont, CA (US)

(73) Assignee: Surromed, Inc., Menlo Park, CA (US)

( * ) Notice: Subject to any disclaimer, the term of this patent is extended or adjusted under 35 U.S.C. 154(b) by 130 days.

(21) Appl. No.: 10/632,694

(22) Filed: Aug. 1, 2003

(65) Prior Publication Data

US 2004/0086515 A1 May 6, 2004

Related U.S. Application Data

(63) Continuation-in-part of application No. 10/080,370, filed on Feb. 21, 2002.
(60) Provisional application No. 60/400,718, filed on Aug. 2, 2002.

(51) Int. Cl.
  *A61K 38/17*  (2006.01)
  *A61K 39/395*  (2006.01)
  *C12P 21/06*  (2006.01)

(52) U.S. Cl. .................. 435/69.1; 424/178.1; 514/12

(58) Field of Classification Search .............. 514/12, 514/8; 424/178.1, 1.69, 9.35; 435/69.1, 212; 530/350
See application file for complete search history.

(56) References Cited

U.S. PATENT DOCUMENTS

| | | | |
|---|---|---|---|
| 4,002,531 A | 1/1977 | Royer | |
| 4,179,337 A | 12/1979 | Davis et al. | |
| 4,507,229 A | 3/1985 | Bohn | |
| 4,732,891 A | 3/1988 | Maki et al. | |
| 4,736,018 A | 4/1988 | Reutelingsperger | |
| 4,897,355 A | 1/1990 | Eppstein et al. | |
| 4,937,324 A | 6/1990 | Fujikawa et al. | |
| 4,965,251 A | * 10/1990 | Stamatoyannopoulos | 514/8 |
| 5,066,787 A | 11/1991 | Reutelingsperger | |
| 5,066,788 A | 11/1991 | Reutelingsperger | |
| 5,097,019 A | 3/1992 | Lobermann et al. | |
| 5,225,537 A | 7/1993 | Foster | |
| 5,290,915 A | 3/1994 | Nakao et al. | |
| 5,296,467 A | 3/1994 | Reutelingsperger | |
| 5,484,711 A | 1/1996 | Wallner et al. | |
| 5,591,633 A | 1/1997 | Saino et al. | |
| 5,608,060 A | 3/1997 | Axworthy et al. | |
| 5,612,460 A | 3/1997 | Zalipsky | |
| 5,632,986 A | * 5/1997 | Tait et al. | 424/94.64 |
| 5,955,437 A | 9/1999 | Reutelingsperger | |
| 5,968,477 A | * 10/1999 | Kasina et al. | 424/1.69 |
| 6,169,078 B1 | 1/2001 | Hughes et al. | |
| 6,171,577 B1 | 1/2001 | Kasina et al. | |
| 6,242,570 B1 | 6/2001 | Sytkowski | |
| 6,312,694 B1 | * 11/2001 | Thorpe et al. | 424/178.1 |
| 6,323,313 B1 | 11/2001 | Tait et al. | |
| 6,358,508 B1 | 3/2002 | Ni et al. | |

2004/0002056 A1    1/2004 Lorens et al.

FOREIGN PATENT DOCUMENTS

| | | |
|---|---|---|
| DE | 19541284 A1 * | 5/1996 |
| WO | WO 95/34315 | 12/1995 |
| WO | WO 97/17084 * | 5/1997 |
| WO | WO9919470 | 4/1999 |
| WO | WO0002587 | 1/2000 |
| WO | WO02087498 | 11/2002 |

OTHER PUBLICATIONS

Allan et al., *Nature* 295:612–613 (1982).
Bangham et al., *J. Mol. Biol.* 23:238–252 (1965).
Behr et al., *Proc. Natl. Acad. Sci. USA* 86:6982–6986 (1989).
Benz and A. Hofmann, *Biol. Chem.* 378:177–183 (1997).
Bernard et al., *Am. Rev. Respir. Dis.* 144:1095–1101 (1991).
Brittain et al., *Blood* 81:22137–2143 (1993).
Burger et al., *FEBS Lett.* 329:25–28 (1993).
Campos et al., *Biochemistry* 37:8004–8010 (1998).
Chow et al., *J. Lab. Clin. Med.* 135:66–72 (2000).
Felgner et al., *Proc. Natl. Acad. Sci. USA* 86: 7413–7417 (1987).
Fritsma, in *Hemostasis and thrombosis in the clinical laboratory* (Corriveau, D.M. and Fritsma, G.A., eds) Lipincott Co., Philadelphia (1989), pp. 92–124.
Fukunaga et al., *Endocrinol.* 115:757 (1984).
Funakoshi et al., *Biochemistry* 26:8087–8092 (1987).
Green et al., *Am. J. Hematol.* 23:317 (1986).
Haupt et al., *Crit. Care Med.* 19:1339–1347 (1991).
Haut et al., *J.Lab. Clin. Med.* 82:44–53 (1973).
Heathcote et al., *N. Engl. J. Med.* 343:1673–1680 (2000).
Hebbel et al., *Abstract. Clin. Res.* 41:762A (1993).
Hermanson, *Bioconjugate techniques.* New York, Academic Press (1996), pp. 173–176.
Huber et al., *EMBO J.* 9:3867–3874 (1990).
Kang et al., *Trends Cardiovasc. Med.* 9:92–102 (1999).
Kaplan et al., *Blood* 57:199–202 (1981).
Kim et al., *Biochem. Biophys. Acta* 728:339 (1983).
Knauf et al., (1988) *J. of Biological Chemistry,* 263:15064–15070.
Kuypers et al., *Blood* 87:1179–1187 (1996).
Lubin et al., *J. Clin. Invest.* 67:1643–1649 (1981).
Mayhew et al., *Biochim. Biophys. Acta* 775:169 (1984).
Meinkoth et al., *Anal. Biochem.* 138:267–284 (1984).
Merten et al., *Circulation* 99:2577–2582 (1999).
Murata et al., *Nature* 388:678–682 (1997).
Olson et al., *Biochim. BIophys. Acta* 557:9 (1979).
Richardson et al., *Br. J. Haematol.* 41:95 (1979).
Rōmisch et al., *Thromb. Res.* 61:93–104 (1991).

(Continued)

Primary Examiner—Jon Weber
Assistant Examiner—Sheridan Snedden
(74) Attorney, Agent, or Firm—Swanson & Bratschun, LLC.

(57) ABSTRACT

Sickle-cell diseases are treated with annexin proteins that are modified to increase their half-life in the circulation.

11 Claims, 3 Drawing Sheets

OTHER PUBLICATIONS

Setty et al., *Blood* 99:1564–1571 (2002).
Stratton et al., *Circulation* 92:3113–3121 (1995).
Strauss et al., *J. Nucl. Med.* 41 (5 Suppl.):149P (2000).
Sugihara et al., *Blood* 80:2634–2642 (1993).
Sun et al., *Thromb. Res.* 69:289–296 (1993).
Szoka, et al., *Proc. Natl. Acad. Sci.* 75:4194 (1978).
Tait et al., *J. Biol. Chem.* 264:7944–7949 (1989).
Thiagarajan and Benedict, *Circulation* 96:2339–2347 (1997).
Thiagagarajan and Tait, *J. Biol. Chem.* 265:17420–17423 (1990).
van Heerde et al., *Arterioscler. Thromb.* 14:824*–830 (1994).
Van Ryn–McKenna et al., *Thromb. Haemost* 69:227–230 (1993).
Veronese et al., *Biomaterials* 22:405 (2001).
Chap et al., Biochem Biophys Res Commun 1988, 150:972–978.
Funakoshi et al., Biochemistry 1987, 26:5572–5578.
Grundmann et al., Behrign Inst Mitt 1988, 82:59–67.
Grundmann et al., Proc Natl Acad Sci USA 1988, 85:3708–3712.
Iwasaki et al., J Biochem (Tokyo) 1987, 102:1261–1273.
Kaplan et al., J. Biol Chem 1988, 263:8037–8043.
Maurer–Fogy et al., Eur J Biochem 1988, 174:585–592.
Nakao et al., Chem Pharm Bull (Tokyo) 1990, 38:1957–1960.
Reutelingsperger et al., Eur J BIochem 1985, 151:625–629.
Reutelingsperger et al., Eur J Biochem 1985, 173:171–178.
Romisch et al., Biochem J 1990, 272:223–229.
Rothhut et al., Biochem J 1989, 263:929–935.
Sytkowski et al. (1998) Proc Natl Acad Sci Usa 95:1184–1188.
Pepinsky et al. (1988) J Biol Chem 263(22):10799–10811.
Kassam et al. (1998)J Biol Chem 273(8):4790–4799.
Zanma et al. (1991) J Biochem 110(6):868–872.
Delgado et al. (1992) Crtical Rev In Therapeutic Drug Carrier Systems 9(3/4):249–304.
Stueber et al. (1995) Peptide Research 8(2):78–85.
Database WPI, Secton Ch, WEeed 200036, Derwent Publications Ltd, London, Shanghai Inst Biochem Chinese Acad (2000) Abstract.
Schlaepfer et al. (1987) Proc. Natl. Acad. Sci. USA 84:6078–6082.
Van Heerde (1994) Arterioscler Thromb 14–824.
Romisch et al. (1991) Thrombosis Research 61:93–104.

* cited by examiner

SEQUENCE LISTING

<160> NUMBER OF SEQ ID NOS: 9

<210> SEQ ID NO 1
<211> LENGTH: 957
<212> TYPE: DNA
<213> ORGANISM: Homo sapiens

<400> SEQUENCE: 1

```
gcacaggttc tcagaggcac tgtgactgac ttccctggat ttgatgagcg ggctgatgca     60
gaaactcttc ggaaggctat gaaaggcttg ggcacagatg aggagagcat cctgactctg    120
ttgacatccc gaagtaatgc tcagcgccag gaaatctctg cagcttttaa gactctgttt    180
ggcagggatc ttctggatga cctgaaatca gaactaactg gaaaatttga aaaattaatt    240
gtggctctga tgaaaccctc tcggctttat gatgcttatg aactgaaaca tgccttgaag    300
ggagctggaa caaatgaaaa agtactgaca gaaattattg cttcaaggac acctgaagaa    360
ctgagagcca tcaaacaagt ttatgaagaa gaatatggct caagcctgga agatgacgtg    420
gtgggggaca cttcagggta ctaccagcgg atgttggtgg ttctccttca ggctaacaga    480
gaccctgatg ctggaattga tgaagctcaa gttgaacaag atgctcaggc tttatttcag    540
gctggagaac ttaaatgggg gacagatgaa gaaaagttta tcaccatctt tggaacacga    600
agtgtgtctc atttgagaaa ggtgtttgac aagtacatga ctatatcagg atttcaaatt    660
gaggaaacca ttgaccgcga gacttctggc aatttagagc aactactcct tgctgttgtg    720
aaatctattc gaagtatacc tgcctacctt gcagagaccc tctattatgc tatgaaggga    780
gctgggacag atgatcatac cctcatcaga gtcatggttt ccaggagtga gattgatctg    840
tttaacatca ggaaggagtt taggaagaat tttgccacct ctctttattc catgattaag    900
ggagatacat ctggggacta taagaaagct cttctgctgc tctgtggaga agatgac      957
```

<210> SEQ ID NO 2
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 2

```
gca cag gtt ctc aga ggc act gtg act gac ttc cct gga ttt gat gag     48
Ala Gln Val Leu Arg Gly Thr Val Thr Asp Phe Pro Gly Phe Asp Glu
1               5                   10                  15 cgg gct gat gca gaa act ctt cgg aag gct atg aaa ggc ttg ggc aca     96
Arg Ala Asp Ala Glu Thr Leu Arg Lys Ala Met Lys Gly Leu Gly Thr
            20                  25                  30 gat gag gag agc atc ctg act ctg ttg aca tcc cga agt aat gct cag    144
Asp Glu Glu Ser Ile Leu Thr Leu Leu Thr Ser Arg Ser Asn Ala Gln
        35                  40                  45 cgc cag gaa atc tct gca gct ttt aag act ctg ttt ggc agg gat ctt    192
Arg Gln Glu Ile Ser Ala Ala Phe Lys Thr Leu Phe Gly Arg Asp Leu
    50                  55                  60 ctg gat gac ctg aaa tca gaa cta act gga aaa ttt gaa aaa tta att    240
```

| | | |
|---|---|---|
| Leu Asp Asp Leu Lys Ser Glu Leu Thr Gly Lys Phe Glu Lys Leu Ile<br>65                        70                    75                    80 | |

```
gtg gct ctg atg aaa ccc tct cgg ctt tat gat gct tat gaa ctg aaa    288
Val Ala Leu Met Lys Pro Ser Arg Leu Tyr Asp Ala Tyr Glu Leu Lys
             85                  90                  95 cat gcc ttg aag gga gct gga aca aat gaa aaa gta ctg aca gaa att    336
His Ala Leu Lys Gly Ala Gly Thr Asn Glu Lys Val Leu Thr Glu Ile
            100                 105                 110 att gct tca agg aca cct gaa gaa ctg aga gcc atc aaa caa gtt tat    384
Ile Ala Ser Arg Thr Pro Glu Glu Leu Arg Ala Ile Lys Gln Val Tyr
        115                 120                 125 gaa gaa gaa tat ggc tca agc ctg gaa gat gac gtg gtg ggg gac act    432
Glu Glu Glu Tyr Gly Ser Ser Leu Glu Asp Asp Val Val Gly Asp Thr
    130                 135                 140 tca ggg tac tac cag cgg atg ttg gtg gtt ctc ctt cag gct aac aga    480
Ser Gly Tyr Tyr Gln Arg Met Leu Val Val Leu Leu Gln Ala Asn Arg
145                 150                 155                 160 gac cct gat gct gga att gat gaa gct caa gtt gaa caa gat gct cag    528
Asp Pro Asp Ala Gly Ile Asp Glu Ala Gln Val Glu Gln Asp Ala Gln
                165                 170                 175 gct tta ttt cag gct gga gaa ctt aaa tgg ggg aca gat gaa gaa aag    576
Ala Leu Phe Gln Ala Gly Glu Leu Lys Trp Gly Thr Asp Glu Glu Lys
            180                 185                 190 ttt atc acc atc ttt gga aca cga agt gtg tct cat ttg aga aag gtg    624
Phe Ile Thr Ile Phe Gly Thr Arg Ser Val Ser His Leu Arg Lys Val
        195                 200                 205 ttt gac aag tac atg act ata tca gga ttt caa att gag gaa acc att    672
Phe Asp Lys Tyr Met Thr Ile Ser Gly Phe Gln Ile Glu Glu Thr Ile
    210                 215                 220 gac cgc gag act tct ggc aat tta gag caa cta ctc ctt gct gtt gtg    720
Asp Arg Glu Thr Ser Gly Asn Leu Glu Gln Leu Leu Leu Ala Val Val
225                 230                 235                 240 aaa tct att cga agt ata cct gcc tac ctt gca gag acc ctc tat tat    768
Lys Ser Ile Arg Ser Ile Pro Ala Tyr Leu Ala Glu Thr Leu Tyr Tyr
                245                 250                 255 gct atg aag gga gct ggg aca gat gat cat acc ctc atc aga gtc atg    816
Ala Met Lys Gly Ala Gly Thr Asp Asp His Thr Leu Ile Arg Val Met
            260                 265                 270 gtt tcc agg agt gag att gat ctg ttt aac atc agg aag gag ttt agg    864
Val Ser Arg Ser Glu Ile Asp Leu Phe Asn Ile Arg Lys Glu Phe Arg
        275                 280                 285 aag aat ttt gcc acc tct ctt tat tcc atg att aag gga gat aca tct    912
Lys Asn Phe Ala Thr Ser Leu Tyr Ser Met Ile Lys Gly Asp Thr Ser
    290                 295                 300 ggg gac tat aag aaa gct ctt ctg ctg ctc tgt gga gaa gat gac        957
Gly Asp Tyr Lys Lys Ala Leu Leu Leu Leu Cys Gly Glu Asp Asp
305                 310                 315

<210> SEQ ID NO 3
<211> LENGTH: 319
<212> TYPE: PRT
<213> ORGANISM: Homo sapiens

<400> SEQUENCE: 3

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45
```

```
Arg Gln Glu Ile Ser Ala Ala Phe Lys Thr Leu Phe Gly Arg Asp Leu
 50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
                100                 105                 110

Ile Ala Ser Arg Thr Pro Glu Glu Leu Arg Ala Ile Lys Gln Val Tyr
                115                 120                 125

Glu Glu Glu Tyr Gly Ser Ser Leu Glu Asp Asp Val Val Gly Asp Thr
            130                 135                 140

Ser Gly Tyr Tyr Gln Arg Met Leu Val Val Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
            195                 200                 205

Phe Asp Lys Tyr Met Thr Ile Ser Gly Phe Gln Ile Glu Glu Thr Ile
210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
                260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
290                 295                 300

Gly Asp Tyr Lys Lys Ala Leu Leu Leu Leu Cys Gly Glu Asp Asp
305                 310                 315
```

<210> SEQ ID NO 4
<211> LENGTH: 2016
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (45)..(45)
<223> OTHER INFORMATION: n = a, c, t, or g
<220> FEATURE:
<221> NAME/KEY: misc_feature
<222> LOCATION: (1000)..(1002)
<223> OTHER INFORMATION: n = a, c, t, or g
<220> FEATURE:
<221> NAME/KEY: misc_feature
<222> LOCATION: (1051)..(1053)
<223> OTHER INFORMATION: n = a, c, t, or g

<400> SEQUENCE: 4

```
atggactaca aagacgatga cgacaagctt gcggccgcga attcngccct gcgcggcacc      60
gtgaccgact ctccggcttc gacggccgc gccgacgccg aggtgctgcg caaggccatg     120
aagggcctgg gcaccgacga ggactccatc ctgaacctgc tgaccgcccg ctccaacgcc    180
```

```
cagcgccagc agatcgccga ggagttcaag accctgttcg gccgcgacct ggtgaacgac      240
atgaagtccg agctgaccgg caagttcgag aagctgatcg tggccctgat gaagccctcc      300
cgcctgtacg acgcctacga gctgaagcac gccaagctgg gcgccggcac cgacgagaag      360
gtgctgaccg agatcatcgc ctcccgcacc cccgaggagc tgcgcgccat caagcaggcc      420
tacgaggagt cgtacggctc caacctggag gacgacgtgg tgggcgacac ctccggctac      480
taccagcgca tgctggtggt gctgctgcag gccaaccgcg accccgacac cgccatcgac      540
gacgcccagg tggagctgga cgcccaggcc ctgttccagg ccggcgagct gaagtggggc      600
accgacgagg agaagttcat caccatcctg ggcacccgct ccgtgtccca cctgcgccgc      660
gtgttcgaca gtacatgac catctccggc ttccagatcg aggagaccat cgaccgcgag      720
acctccggca acctggagaa cctgctgctg gccgtggtga agtccatccg ctccatcccc      780
gcctacctgg ccgagaccct gtactacgcc atgaagggcg ccggcaccga cgaccacacc      840
ctgatccgcg tgatcgtgtc ccgctccgag atcgacctgt tcaacatccg caaggagttc      900
cgcaagaact tcgccacctc cctgtactcc atgatcaagg gcgacacctc cggcgactac      960
aagaaggccc tgctgctgct gtgcggcggc gaggacgacn nnagatctcg atcgggcctg    1020
gaggtgctgt tccagggccc cggaagtact nnngccctgc gcggcaccgt gaccgacttc    1080
tccggcttcg acggccgcgc cgacgccgag gtgctgcgca aggccatgaa gggcctgggc    1140
accgacgagg actccatcct gaacctgctg accgcccgct ccaacgccca gcgccagcag    1200
atcgccgagg agttcaagac cctgttcggc cgcgacctgg tgaacgacat gaagtccgag    1260
ctgaccggca gttcgagaa gctgatcgtg gccctgatga agccctccg cctgtacgac    1320 gcctacgagc tgaagcacgc caagctgggc gccggcaccg acgagaaggt gctgaccgag    1380
atcatcgcct cccgcacccc cgaggagctg cgcgccatca gcaggccta cgaggaggag    1440 tacggctcca acctggagga cgacgtggtg gcgacacct ccggctacta ccagcgcatg    1500
ctggtggtgc tgctgcaggc caaccgcgac cccgacaccg ccatcgacga cgcccaggtg    1560
gagctggacg cccaggccct gttccaggcc ggcgagctga agtggggcac cgacgaggag    1620
aagttcatca ccatcctggg cacccgctcc gtgtcccacc tgcgccgcgt gttcgacaag    1680
tacatgacca tctccggctt ccagatcgag gagaccatcg accgcgagac ctccggcaac    1740
ctggagaacc tgctgctggc cgtggtgaag tccatccgct ccatcccgc ctacctggcc    1800 gagaccctgt actacgccat gaagggcgcc ggcaccgacg accacaccct gatccgcgtg    1860
atcgtgtccc gctccgagat cgacctgttc aacatccgca aggagttccg caagaacttc    1920
gccacctccc tgtactccat gatcaagggc gacacctccg gcgactacaa gaaggccctg    1980
ctgctgctgt gcggcggcga ggacgactaa taataa                               2016
```

<210> SEQ ID NO 5
<211> LENGTH: 2016
<212> TYPE: DNA
<213> ORGANISM: Artificial Sequence
<220> FEATURE:
<223> OTHER INFORMATION: primer
<220> FEATURE:
<221> NAME/KEY: CDS
<222> LOCATION: (1)..(2016)
<220> FEATURE:
<221> NAME/KEY: misc_feature
<222> LOCATION: (45)..(45)
<223> OTHER INFORMATION: n = a, c, t, or g
<220> FEATURE:
<221> NAME/KEY: misc_feature
<222> LOCATION: (1000)..(1002)
<223> OTHER INFORMATION: n = a, c, t, or g
<220> FEATURE:
<221> NAME/KEY: misc_feature
<222> LOCATION: (1051)..(1053)
<223> OTHER INFORMATION: n = a, c, t, or g

<400> SEQUENCE: 5

```
atg gac tac aaa gac gat gac gac aag ctt gcg gcc gcg aat tcn gcc      48
Met Asp Tyr Lys Asp Asp Asp Asp Lys Leu Ala Ala Ala Asn Xaa Ala
1               5                  10                  15 ctg cgc ggc acc gtg acc gac ttc tcc ggc ttc gac ggc cgc gcc gac      96
Leu Arg Gly Thr Val Thr Asp Phe Ser Gly Phe Asp Gly Arg Ala Asp
            20                  25                  30 gcc gag gtg ctg cgc aag gcc atg aag ggc ctg ggc acc gac gag gac     144
Ala Glu Val Leu Arg Lys Ala Met Lys Gly Leu Gly Thr Asp Glu Asp
        35                  40                  45 tcc atc ctg aac ctg ctg acc gcc cgc tcc aac gcc cag cgc cag cag     192
Ser Ile Leu Asn Leu Leu Thr Ala Arg Ser Asn Ala Gln Arg Gln Gln
    50                  55                  60 atc gcc gag gag ttc aag acc ctg ttc ggc cgc gac ctg gtg aac gac     240
Ile Ala Glu Glu Phe Lys Thr Leu Phe Gly Arg Asp Leu Val Asn Asp
65                  70                  75                  80 atg aag tcc gag ctg acc ggc aag ttc gag aag ctg atc gtg gcc ctg     288
Met Lys Ser Glu Leu Thr Gly Lys Phe Glu Lys Leu Ile Val Ala Leu
                85                  90                  95 atg aag ccc tcc cgc ctg tac gac gcc tac gag ctg aag cac gcc aag     336
Met Lys Pro Ser Arg Leu Tyr Asp Ala Tyr Glu Leu Lys His Ala Lys
            100                 105                 110 ctg ggc gcc ggc acc gac gag aag gtg ctg acc gag atc atc gcc tcc     384
Leu Gly Ala Gly Thr Asp Glu Lys Val Leu Thr Glu Ile Ile Ala Ser
        115                 120                 125 cgc acc ccc gag gag ctg cgc gcc atc aag cag gcc tac gag gag gag     432
Arg Thr Pro Glu Glu Leu Arg Ala Ile Lys Gln Ala Tyr Glu Glu Glu
    130                 135                 140 tac ggc tcc aac ctg gag gac gac gtg gtg ggc gac acc tcc ggc tac     480
Tyr Gly Ser Asn Leu Glu Asp Asp Val Val Gly Asp Thr Ser Gly Tyr
145                 150                 155                 160 tac cag cgc atg ctg gtg gtg ctg ctg cag gcc aac cgc gac ccc gac     528
Tyr Gln Arg Met Leu Val Val Leu Leu Gln Ala Asn Arg Asp Pro Asp
                165                 170                 175 acc gcc atc gac gac gcc cag gtg gag ctg gac gcc cag gcc ctg ttc     576
Thr Ala Ile Asp Asp Ala Gln Val Glu Leu Asp Ala Gln Ala Leu Phe
            180                 185                 190 cag gcc ggc gag ctg aag tgg ggc acc gac gag gag aag ttc atc acc     624
Gln Ala Gly Glu Leu Lys Trp Gly Thr Asp Glu Glu Lys Phe Ile Thr
        195                 200                 205 atc ctg ggc acc cgc tcc gtg tcc cac ctg cgc cgc gtg ttc gac aag     672
Ile Leu Gly Thr Arg Ser Val Ser His Leu Arg Arg Val Phe Asp Lys
    210                 215                 220 tac atg acc atc tcc ggc ttc cag atc gag gag acc atc gac cgc gag     720
Tyr Met Thr Ile Ser Gly Phe Gln Ile Glu Glu Thr Ile Asp Arg Glu
225                 230                 235                 240 acc tcc ggc aac ctg gag aac ctg ctg ctg gcc gtg gtg aag tcc atc     768
Thr Ser Gly Asn Leu Glu Asn Leu Leu Leu Ala Val Val Lys Ser Ile
                245                 250                 255 cgc tcc atc ccc gcc tac ctg gcc gag acc ctg tac tac gcc atg aag     816
Arg Ser Ile Pro Ala Tyr Leu Ala Glu Thr Leu Tyr Tyr Ala Met Lys
            260                 265                 270 ggc gcc ggc acc gac gac cac acc ctg atc cgc gtg atc gtg tcc cgc     864
Gly Ala Gly Thr Asp Asp His Thr Leu Ile Arg Val Ile Val Ser Arg
```

-continued

```
                 275                 280                 285
tcc gag atc gac ctg ttc aac atc cgc aag gag ttc cgc aag aac ttc        912
Ser Glu Ile Asp Leu Phe Asn Ile Arg Lys Glu Phe Arg Lys Asn Phe
    290                 295                 300 gcc acc tcc ctg tac tcc atg atc aag ggc gac acc tcc ggc gac tac        960
Ala Thr Ser Leu Tyr Ser Met Ile Lys Gly Asp Thr Ser Gly Asp Tyr
305                 310                 315                 320 aag aag gcc ctg ctg ctg ctg tgc ggc ggc gag gac gac nnn aga tct       1008
Lys Lys Ala Leu Leu Leu Leu Cys Gly Gly Glu Asp Asp Xaa Arg Ser
                325                 330                 335 cga tcg ggc ctg gag gtg ctg ttc cag ggc ccc gga agt act nnn gcc       1056
Arg Ser Gly Leu Glu Val Leu Phe Gln Gly Pro Gly Ser Thr Xaa Ala
                340                 345                 350 ctg cgc ggc acc gtg acc gac ttc tcc ggc ttc gac ggc cgc gcc gac       1104
Leu Arg Gly Thr Val Thr Asp Phe Ser Gly Phe Asp Gly Arg Ala Asp
                355                 360                 365 gcc gag gtg ctg cgc aag gcc atg aag ggc ctg ggc acc gac gag gac       1152
Ala Glu Val Leu Arg Lys Ala Met Lys Gly Leu Gly Thr Asp Glu Asp
                370                 375                 380 tcc atc ctg aac ctg ctg acc gcc cgc tcc aac gcc cag cgc cag cag       1200
Ser Ile Leu Asn Leu Leu Thr Ala Arg Ser Asn Ala Gln Arg Gln Gln
385                 390                 395                 400 atc gcc gag gag ttc aag acc ctg ttc ggc cgc gac ctg gtg aac gac       1248
Ile Ala Glu Glu Phe Lys Thr Leu Phe Gly Arg Asp Leu Val Asn Asp
                405                 410                 415 atg aag tcc gag ctg acc ggc aag ttc gag aag ctg atc gtg gcc ctg       1296
Met Lys Ser Glu Leu Thr Gly Lys Phe Glu Lys Leu Ile Val Ala Leu
                420                 425                 430 atg aag ccc tcc cgc ctg tac gac gcc tac gag ctg aag cac gcc aag       1344
Met Lys Pro Ser Arg Leu Tyr Asp Ala Tyr Glu Leu Lys His Ala Lys
                435                 440                 445 ctg ggc gcc ggc acc gac gag aag gtg ctg acc gag atc atc gcc tcc       1392
Leu Gly Ala Gly Thr Asp Glu Lys Val Leu Thr Glu Ile Ile Ala Ser
450                 455                 460 cgc acc ccc gag gag ctg cgc gcc atc aag cag gcc tac gag gag gag       1440
Arg Thr Pro Glu Glu Leu Arg Ala Ile Lys Gln Ala Tyr Glu Glu Glu
465                 470                 475                 480 tac ggc tcc aac ctg gag gac gac gtg gtg ggc gac acc tcc ggc tac       1488
Tyr Gly Ser Asn Leu Glu Asp Asp Val Val Gly Asp Thr Ser Gly Tyr
                485                 490                 495 tac cag cgc atg ctg gtg gtg ctg ctg cag gcc aac cgc gac ccc gac       1536
Tyr Gln Arg Met Leu Val Val Leu Leu Gln Ala Asn Arg Asp Pro Asp
                500                 505                 510 acc gcc atc gac gac gcc cag gtg gag ctg gac gcc cag gcc ctg ttc       1584
Thr Ala Ile Asp Asp Ala Gln Val Glu Leu Asp Ala Gln Ala Leu Phe
                515                 520                 525 cag gcc ggc gag ctg aag tgg ggc acc gac gag gag aag ttc atc acc       1632
Gln Ala Gly Glu Leu Lys Trp Gly Thr Asp Glu Glu Lys Phe Ile Thr
530                 535                 540 atc ctg ggc acc cgc tcc gtg tcc cac ctg cgc cgc gtg ttc gac aag       1680
Ile Leu Gly Thr Arg Ser Val Ser His Leu Arg Arg Val Phe Asp Lys
545                 550                 555                 560 tac atg acc atc tcc ggc ttc cag atc gag gag acc atc gac cgc gag       1728
Tyr Met Thr Ile Ser Gly Phe Gln Ile Glu Glu Thr Ile Asp Arg Glu
                565                 570                 575 acc tcc ggc aac ctg gag aac ctg ctg ctg gcc gtg gtg aag tcc atc       1776
Thr Ser Gly Asn Leu Glu Asn Leu Leu Leu Ala Val Val Lys Ser Ile
                580                 585                 590 cgc tcc atc ccc gcc tac ctg gcc gag acc ctg tac tac gcc atg aag       1824
```

```
                                                                                   -continued Arg Ser Ile Pro Ala Tyr Leu Ala Glu Thr Leu Tyr Tyr Ala Met Lys
        595                 600                 605 ggc gcc ggc acc gac gac cac acc ctg atc cgc gtg atc gtg tcc cgc          1872
Gly Ala Gly Thr Asp Asp His Thr Leu Ile Arg Val Ile Val Ser Arg
    610                 615                 620 tcc gag atc gac ctg ttc aac atc cgc aag gag ttc cgc aag aac ttc          1920
Ser Glu Ile Asp Leu Phe Asn Ile Arg Lys Glu Phe Arg Lys Asn Phe
625                 630                 635                 640 gcc acc tcc ctg tac tcc atg atc aag ggc gac acc tcc ggc gac tac          1968
Ala Thr Ser Leu Tyr Ser Met Ile Lys Gly Asp Thr Ser Gly Asp Tyr
                645                 650                 655 aag aag gcc ctg ctg ctg ctg tgc ggc ggc gag gac gac taa taa taa          2016
Lys Lys Ala Leu Leu Leu Leu Cys Gly Gly Glu Asp Asp
            660                 665

<210> SEQ ID NO 6
<211> LENGTH: 669
<212> TYPE: PRT
<213> ORGANISM: Artificial Sequence
<220> FEATURE:
<221> NAME/KEY: misc_feature
<222> LOCATION: (15)..(15)
<223> OTHER INFORMATION: The 'Xaa' at location 15 stands for Ser.
<220> FEATURE:
<221> NAME/KEY: misc_feature
<222> LOCATION: (334)..(334)
<223> OTHER INFORMATION: The 'Xaa' at location 334 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (351)..(351)
<223> OTHER INFORMATION: The 'Xaa' at location 351 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: primer

<400> SEQUENCE: 6

Met Asp Tyr Lys Asp Asp Asp Lys Leu Ala Ala Ala Asn Xaa Ala
1               5                   10                  15

Leu Arg Gly Thr Val Thr Asp Phe Ser Gly Phe Asp Gly Arg Ala Asp
            20                  25                  30

Ala Glu Val Leu Arg Lys Ala Met Lys Gly Leu Gly Thr Asp Glu Asp
        35                  40                  45

Ser Ile Leu Asn Leu Leu Thr Ala Arg Ser Asn Ala Gln Arg Gln Gln
    50                  55                  60

Ile Ala Glu Glu Phe Lys Thr Leu Phe Gly Arg Asp Leu Val Asn Asp
65                  70                  75                  80

Met Lys Ser Glu Leu Thr Gly Lys Phe Glu Lys Leu Ile Val Ala Leu
                85                  90                  95

Met Lys Pro Ser Arg Leu Tyr Asp Ala Tyr Glu Leu Lys His Ala Lys
            100                 105                 110

Leu Gly Ala Gly Thr Asp Glu Lys Val Leu Thr Glu Ile Ile Ala Ser
        115                 120                 125

Arg Thr Pro Glu Glu Leu Arg Ala Ile Lys Gln Ala Tyr Glu Glu Glu
    130                 135                 140

Tyr Gly Ser Asn Leu Glu Asp Asp Val Val Gly Asp Thr Ser Gly Tyr
145                 150                 155                 160

Tyr Gln Arg Met Leu Val Val Leu Leu Gln Ala Asn Arg Asp Pro Asp
                165                 170                 175

Thr Ala Ile Asp Asp Ala Gln Val Glu Leu Asp Ala Gln Ala Leu Phe
```

-continued

```
                180                 185                 190
Gln Ala Gly Glu Leu Lys Trp Gly Thr Asp Glu Lys Phe Ile Thr
            195                 200                 205
Ile Leu Gly Thr Arg Ser Val Ser His Leu Arg Arg Val Phe Asp Lys
        210                 215                 220
Tyr Met Thr Ile Ser Gly Phe Gln Ile Glu Glu Thr Ile Asp Arg Glu
225                 230                 235                 240
Thr Ser Gly Asn Leu Glu Asn Leu Leu Leu Ala Val Val Lys Ser Ile
                245                 250                 255
Arg Ser Ile Pro Ala Tyr Leu Ala Glu Thr Leu Tyr Tyr Ala Met Lys
            260                 265                 270
Gly Ala Gly Thr Asp Asp His Thr Leu Ile Arg Val Ile Val Ser Arg
        275                 280                 285
Ser Glu Ile Asp Leu Phe Asn Ile Arg Lys Glu Phe Arg Lys Asn Phe
        290                 295                 300
Ala Thr Ser Leu Tyr Ser Met Ile Lys Gly Asp Thr Ser Gly Asp Tyr
305                 310                 315                 320
Lys Lys Ala Leu Leu Leu Cys Gly Gly Glu Asp Asp Xaa Arg Ser
                325                 330                 335
Arg Ser Gly Leu Glu Val Leu Phe Gln Gly Pro Gly Ser Thr Xaa Ala
            340                 345                 350
Leu Arg Gly Thr Val Thr Asp Phe Ser Gly Phe Asp Gly Arg Ala Asp
        355                 360                 365
Ala Glu Val Leu Arg Lys Ala Met Lys Gly Leu Gly Thr Asp Glu Asp
370                 375                 380
Ser Ile Leu Asn Leu Leu Thr Ala Arg Ser Asn Ala Gln Arg Gln Gln
385                 390                 395                 400
Ile Ala Glu Glu Phe Lys Thr Leu Phe Gly Arg Asp Leu Val Asn Asp
            405                 410                 415
Met Lys Ser Glu Leu Thr Gly Lys Phe Glu Lys Leu Ile Val Ala Leu
        420                 425                 430
Met Lys Pro Ser Arg Leu Tyr Asp Ala Tyr Glu Leu Lys His Ala Lys
        435                 440                 445
Leu Gly Ala Gly Thr Asp Glu Lys Val Leu Thr Glu Ile Ile Ala Ser
    450                 455                 460
Arg Thr Pro Glu Glu Leu Arg Ala Ile Lys Gln Ala Tyr Glu Glu Glu
465                 470                 475                 480
Tyr Gly Ser Asn Leu Glu Asp Asp Val Val Gly Asp Thr Ser Gly Tyr
                485                 490                 495
Tyr Gln Arg Met Leu Val Val Leu Leu Gln Ala Asn Arg Asp Pro Asp
            500                 505                 510
Thr Ala Ile Asp Asp Ala Gln Val Glu Leu Asp Ala Gln Ala Leu Phe
        515                 520                 525
Gln Ala Gly Glu Leu Lys Trp Gly Thr Asp Glu Lys Phe Ile Thr
    530                 535                 540
Ile Leu Gly Thr Arg Ser Val Ser His Leu Arg Arg Val Phe Asp Lys
545                 550                 555                 560
Tyr Met Thr Ile Ser Gly Phe Gln Ile Glu Glu Thr Ile Asp Arg Glu
                565                 570                 575
Thr Ser Gly Asn Leu Glu Asn Leu Leu Leu Ala Val Val Lys Ser Ile
            580                 585                 590
Arg Ser Ile Pro Ala Tyr Leu Ala Glu Thr Leu Tyr Tyr Ala Met Lys
        595                 600                 605
```

```
Gly Ala Gly Thr Asp Asp His Thr Leu Ile Arg Val Ile Val Ser Arg
    610                 615                 620

Ser Glu Ile Asp Leu Phe Asn Ile Arg Lys Glu Phe Arg Lys Asn Phe
625                 630                 635                 640

Ala Thr Ser Leu Tyr Ser Met Ile Lys Gly Asp Thr Ser Gly Asp Tyr
                645                 650                 655

Lys Lys Ala Leu Leu Leu Leu Cys Gly Gly Glu Asp Asp
            660                 665

<210> SEQ ID NO 7
<211> LENGTH: 30
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(30)
<223> OTHER INFORMATION: primer

<400> SEQUENCE: 7
acctgagtag tcgccatggc acaggttctc                                        30

<210> SEQ ID NO 8
<211> LENGTH: 36
<212> TYPE: DNA
<213> ORGANISM: artificial sequence
<220> FEATURE:
<223> OTHER INFORMATION: primer

<400> SEQUENCE: 8
cccgaattca cgttagtcat cttctccaca gagcag                                 36

<210> SEQ ID NO 9
<211> LENGTH: 8
<212> TYPE: PRT
<213> ORGANISM: Artificial
<220> FEATURE:
<223> OTHER INFORMATION: synthetic fusion peptide

<400> SEQUENCE: 9

Asp Tyr Lys Asp Asp Asp Asp Lys
1               5
```

MODIFIED ANNEXIN PROTEINS AND METHODS FOR TREATING VASO-OCCLUSIVE SICKLE-CELL DISEASE

CROSS-REFERENCE TO RELATED APPLICATIONS

This application claims priority from U.S. Provisional Application No. 60/400,718, "Therapy for Vaso-Occlusive Sickle-Cell Disease," filed Aug. 2, 2002, which is incorporated herein by reference. This application is a continuation-in-part of U.S. application Ser. No. 10/080,370, "Modified Annexin Proteins and Methods for Preventing Thrombosis," filed Feb. 21, 2002, which is incorporated herein by reference.

FIELD OF THE INVENTION

The present invention relates generally to methods and compositions for treating blood disorders. More particularly, it relates to modified annexin proteins used to treat vaso-occlusive sickle-cell disease.

BACKGROUND OF THE INVENTION

Sickle-cell diseases are a class of genetic disorders caused by a point mutation that leads to a structural abnormality of hemoglobin in red blood cells. When deoxygenated, the abnormal hemoglobin, HbS, polymerizes, resulting in the characteristic sickle shape of the red blood cell. Sickled cells lack the pliability required to traverse small capillaries and have an increased propensity to adhere to endothelial cells of blood vessels. Patients with sickle-cell anemia are homozygous for the sickle-cell gene (SS); other forms of the disease, which may be less severe, occur in patients who have both the sickle-cell gene and a gene for another hemoglobinopathy, such as β-thalassemia or other mutant hemoglobins (e.g., C or D).

An estimated 70,000 Americans have sickle-cell disease, making it the most common simply inherited disorder in the US. The clinical manifestations of sickle-cell disease vary widely among patients, in both affected organ systems and symptom severity. Morbidity and mortality are generally related to vaso-occlusive complications, including pain crises, acute chest syndrome, osteonecrosis, and splenic infarction and consquent infection. Patients also suffer from increased risk of stroke and cerebral hemorrhage.

Currently, sickle-cell disease is treated with hydroxyurea, with analgesics for pain, or, less commonly, by bone marrow transplantation. Hydroxyurea induces production of fetal hemoglobin, which retards sickling, increases the red blood cell volume, and reduces the number of dense and irreversibly sickled cells in the circulation. It does not cure the disease and must be administered continuously throughout the lifetime of the patient. Bone marrow transplantation can cure the disease but may have potentially fatal side effects. It is also difficult to locate a properly matched donor. Clearly, additional therapies are needed.

SUMMARY OF THE INVENTION

The present invention provides compounds and methods for treating sickle-cell disease. A recombinant human annexin, preferably annexin V, is modified in such a way that its half-life in the vascular compartment is prolonged. This can be achieved in a variety of ways; three embodiments are an annexin coupled to polyethylene glycol, a homopolymer or heteropolymer of annexin, and a fusion protein of annexin with another protein (e.g., the Fc portion of immunoglobulin). The modified annexin binds with high affinity to phosphatidylserine (PS) on the surface of sickle cells and activated platelets. The former prevents binding of sickle cells to endothelial cells, whereas the latter prevents the formation of a prothrombinase complex, thereby preventing thrombosis. In addition, modified annexin binds to PS on sickled red blood cells and microvesicles, preventing adhesion to endothelial cells and inhibiting the activity of secretory phospholipase $A_2$ ($sPLA_2$). This prevents the formation of mediators producing pain and contributing to pulmonary pathology.

In one embodiment, the present invention provides an isolated modified annexin protein containing an annexin protein, such as annexin V, coupled to polyethylene glycol (PEG). Preferably, at least two PEG chains are coupled to a single annexin molecule, with each PEG having a molecular weight of at least 10 kDa or at least 20 kDa. In an alternative embodiment, an isolated modified annexin protein contains an annexin protein coupled to at least one additional protein, such as an additional annexin protein (forming a homodimer) or the Fc portion of immunoglobulin. The additional protein typically has a molecular weight of at least 35 kDa. Also provided by the present invention are pharmaceutical compositions containing a therapeutically effective amount of any of the modified annexin proteins of the invention.

In methods of the invention, the modified annexin is administered to a subject at risk of a sickle-cell crisis in a pharmaceutical composition having an effective amount of any one of the modified annexin proteins of the present invention. For example, the pharmaceutical composition can be administered early in the course of a sickle-cell crisis, or when a biomarker shows that the patient is likely to develop the acute lung syndrome that is a serious complication of sickle-cell disease. The modified annexin may decrease the severity of pain, vaso-occlusion, or lung pathology.

In an alternative embodiment, the modified annexin can be administered to a sickle-cell patient with cerebral thrombosis to decrease the likelihood of further thrombosis and reperfusion injury.

Also provided by the present invention are an isolated nucleic acid molecule encoding a homodimer of annexin, a recombinant molecule containing at least a portion of the nucleic acid molecule, and a recombinant cell containing at least a portion of the nucleic acid molecule. The recombinant cell is cultured under suitable conditions in a method of the invention to produce a homodimer of annexin.

The present invention also provides a method for screening for a modified annexin protein that modulates thrombosis using a thrombosis test system. The test system is contacted with a modified annexin protein, after which the thrombotic activity is assessed and compared with the activity of the system in the absence of the test-modified annexin protein. Preferably, the activated partial thromboplastin time is measured. An alternative embodiment is a method for screening for a modified annexin protein that inhibits $sPLA_2$ activity on red blood cells or microvesicles. The PS-exposing red blood cells are contacted with a test-modified annexin protein in the presence of $sPLA_2$, and the hydrolytic activity of $sPLA_2$ is compared in the presence and absence of the test-modified annexin protein.

Also provided by the present invention are methods for in vivo screening for activities of a modified annexin protein. In one method, the modified annexin is injected into mice transgenically expressing human sickle-cell hemoglobin. In such mice, the lifespan of red blood cells is shortened, and test-modified annexin is expected to prolong their lifespan. Thrombosis contributes to the pathogenesis of sickle-cell disease, and so in a second model, the antithrombotic activity of modified annexins is assessed. At different times after injection of the test-modified annexin into rats, lesions are produced in mesenteric blood vessels. The lesions are prothrombotic, and modified annexins attenuate such effects.

DETAILED DESCRIPTION OF THE INVENTION

Figure 1:
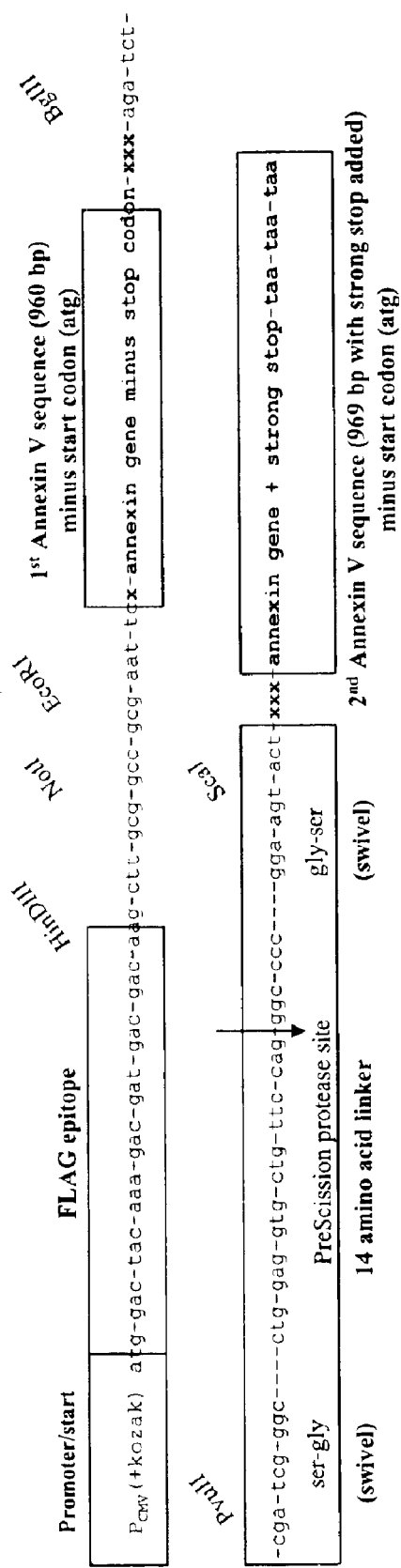
FIG. 1 shows a DNA construct for making a homodimer of annexin V.

Various embodiments of the present invention provide methods and compositions for treating sickle-cell disease in a patient. A homodimer or heterodimer of annexin (e.g., annexin V), produced by genetic or chemical methods, is administered to the patient and is effective in treating pain crises, vaso-occlusive crises, and acute chest syndrome, as well as other aspects of the disease or related diseases. In another embodiment, a conjugate of annexin with polyethylene glycol or another polymer is used for the same purpose.

Annexin V binds phosphatidylserine (PS) on the surface of activated platelets and other cell types that have lost plasma membrane phospholipid asymmetry. This occurs on some red blood cells as they become sickled when deoxygenated, producing procoagulant microvesicles and mediators of pain. PS on the surface of sickle cells is a major mediator of their adhesion to endothelial cells, which contributes to vaso-occlusion. Agglutinated platelets and sickle cells interact to form vaso-occlusive plugs, a process that can be prevented at least in part by annexin V binding. The native form of annexin V has a molecular weight of approximately 35 kDa and so is rapidly removed from the circulation into the urine. In embodiments of the present invention, an annexin dimer or a conjugate of annexin with another protein or a polymer is administered. In comparison with the native annexin molecule, the higher-molecular weight conjugate has a prolonged circulation time with consequent greater efficacy in treating sickle-cell disease. Unlike other antithrombotic agents, annexin can inhibit platelet aggregation without increasing hemorrhage.

The annexins are a family of homologous phospholipid-binding proteins, of which ten represent distinct gene products expressed in mammals. Crystallographic analysis has revealed a common tertiary structure for all the family members so far studied, exemplified by annexin V (R. Huber et al., *EMBO J.* 9:3867–3874 (1990)). The core domain is a concave discoid structure that can be closely apposed to phospholipid membranes. It contains four subdomains, each consisting of a 70-amino-acid annexin repeat made up of five α-helices. The annexins also have a more hydrophilic tail domain that varies in length and amino acid sequence among the different annexins. The sequences of genes encoding annexins are well known (e.g., annexin V, T. Funakoshi et al., *Biochemistry* 26:8087–8092 (1987)).

In embodiments of the present invention, annexin proteins are modified to increase their half-life in the circulation of humans or other mammals. In one embodiment, the annexin protein is annexin V. One suitable modification of annexin is an increase in its effective size, which prevents loss from the vascular compartment into the extravascular compartment and urine, thereby prolonging efficacy in treating sickle-cell disease and other disorders or conditions following a single injection. Any increase in effective size that maintains a sufficient binding affinity with PS is within the scope of the present invention.

Compounds employed in different embodiments of the present invention include any product containing annexin amino-acid sequences that have been modified to increase the half-life of the product in humans or other mammals. Where "amino-acid sequence" is recited herein to refer to an amino-acid sequence of a naturally-occurring protein molecule, "amino-acid sequence" and like terms, such as "polypeptide" or "protein," are not meant to limit the amino-acid sequence to the complete, native amino-acid sequence associated with the recited proteins.

To inhibit the aggregation of platelets and formation of vaso-occlusive plugs without increasing hemorrhage, it is necessary to exploit potential differences between mechanisms involved in hemostasis and those involved in platelet aggregation and other mechanisms causing vaso-occlusive crisis. Primary hemostatic mechanisms include the formation of platelet microaggregates, which plug capillaries and accumulate over damaged or activated endothelial cells in small blood vessels. Occlusion by a thrombus requires the continued recruitment and incorporation of platelets into the thrombus. To overcome detachment by shear forces in large blood vessels, platelets must be bound tightly to one another and to the fibrin network deposited around them.

It is to be understood that the mechanisms described below are not definitive, and that embodiments of the present invention are not limited to the disclosed mechanisms.

The pathogenesis of sickle-cell disease in general and vaso-occlusive crises in particular is complex. Annexin can inhibit a variety of different disease mechanisms in which phosphatidylserine (PS) is exposed on cell surfaces. In oxygenated red blood cells from patients with sickle-cell disease, PS is confined to the inner leaflet of the plasma membrane bilayer (K. Sugihara et al., *Blood* 80:2634–2642 (1992)). When these cells are deoxygenated, phospholipid asymmetry is lost and PS becomes accessible on the outer leaflet of the membrane bilayer (B. Lubin et al., *J. Clin. Invest.* 67:1643–1649 (1981)). This loss of phospholipid asymmetry in sickled red blood cells remains when the cells are reoxygenated. Binding of fluorescently-labeled annexin V to red blood cells is substantially higher in sickle-cell patients than in normal humans, indicating a greater degree of PS exposure on the cell surface (F. A. Kuypers et al., *Blood* 87:1179–1187 (1996)). Exposed PS facilitates adhesion of red blood cells to endothelial cells of blood vessels, impeding blood flow (B. N. Y. Setty et al., *Blood* 99:1564–1571 (2002)). Although only about 2% of circulating red blood cells are annexin-labeled in sickle-cell patients, many may be removed from the circulation by binding to endothelial cells. When deoxygenated, red blood cells of patients with sickle-cell disease also shed microvesicles containing phospholipids (D. Allan et al., *Nature* 295:612–613 (1982); and B. Lubin et al., *J. Clin. Invest.* 67:1643–1649 (1981)). By adhering to PS on the surface of red blood cells and microvesicles, modified annexin may prevent adhesion of the red blood cells and microvesicles to endothelial cells and the resulting vaso-occlusive effects.

These events are further amplified by the aggregation of activated platelets and their adhesion to red blood cells and endothelial cells. Patients with sickle-cell disease exhibit increased platelet activation. For example, increased levels of β-thromboglobulin and platelet factor 4, both of which are involved in platelet activation, have been found in the circulation of patients with sickle-cell disease (D. Green et al., *Am. J. Hematol.* 23:317 (1986); and K. L. Kaplan et al., *Blood* 57:199–202 (1981)). Urinary levels of thromboxane $B_2$ are also increased (B. O. Ibe et al., Eighteenth Annual Meeting of the National Sickle-Cell Disease Program 76a (1993)). During acute painful sickle-cell episodes, reduced platelet counts, shortened platelet survival, and release of thrombospondin from platelets have all been observed (M. J. Haut et al., *J. Lab. Clin. Med.* 82:44–53 (1973); S. G. N. Richardson et al., *Br. J. Haematol.* 41:95 (1979); and R. P. Hebbel et al., *Abstract. Clin. Res.* 41:762A (1993)). Thrombospondin binds to the surface of sickle cells, particularly CD36+ reticulocytes, and increases their attachment to endothelial cells (K. Sugihara et al., *Blood* 80:2634–2642 (1992); H. A. Brittain et al., *Blood* 81:2137–2143 (1993)). Aggregates of platelets and red blood cells that adhere to endothelial cells form microthrombi, further obstructing blood flow and contributing to cerebral thrombosis, impaired mental function, and disorders of the spleen. In embodiments of the present invention, modified annexin inhibits both adhesion to endothelial cells and platelet aggregation.

During aggregation, platelets release secretory phospholipase $A_2$ ($sPLA_2$), an enzyme that attacks surface-accessible PS on microvesicles and red blood cells to generate lysophosphatidic acid (LPA), which induces further platelet activation; lysophosphatidylcholine (LPC), to which C-reactive protein binds, activating complement and recruiting leukocytes, and arachidonic acid (AA), which is metabolized to prostanoids such as prostaglandins. Some prostanoids (e.g., thromboxane $A_2$, a vasoconstrictor and promoter of platelet aggregation) are prothrombotic, while others (e.g., $PGE_2$, a vasodilator with immunosuppressive effects on leukotrienes) are co-factors in the induction of pain. For example, mice lacking receptors for prostacyclin exhibit reduced pain responses (T. Murata et al., *Nature* 388:678–682 (1997)). Complement activation is linked with the formation of kinins, which are co-mediators of pain. Preventing access of $sPLA_2$ to PS by annexin binding can prevent the production of these and other pain mediators and thereby diminish the pain associated with vaso-occlusive crises.

Prostaglandins generated from surface-accessible PS may also contribute to Acute Chest Syndrome (ACS), the leading cause of death among patients with sickle-cell disease. The cause of ACS is largely unknown, but is believed to be a combination of pulmonary fat embolism and a variety of infectious pathogens. Patients with sickle-cell disease have been shown to have levels of $sPLA_2$ that are markedly elevated and correlated with severity of the acute chest syndrome. The same correlation is found in Acute (or Adult) Respiratory Distress Syndrome (ARDS), a lung dysfunction associated with a variety of diseases. Prostaglandins include both vasoconstrictors and vasodilators, and it is believed that some of these may contribute to or aggravate development of the chest syndrome. In ARDS, studies have shown clinical benefits in reducing levels of thromboxane $A_2$, $PGE_2$, and prostacyclin (G. R. Bernard et al., *Am. Rev. Respir. Dis.* 144:1095–1101 (1991); and M. Haupt et al., *Crit. Care Med.* 19:1339–1347 (1991)). In embodiments of the present invention, modified annexin may inhibit production of these prostanoids and slow the progression or inhibit the development of the acute chest syndrome.

Platelet aggregation also plays a role in the pathogenesis of sickle-ell disease. Splenic thrombosis often leads to autosplenectomy, which increases susceptibility to some bacterial infections. Cerebral thrombosis is much more frequent in patients with sickle-cell disease than in other humans of the same age. Co-aggregates of platelets and red cells are thought to play a major role in the pathogenesis of vaso-occlusion. In sickle-cell disease it is important to prevent thrombosis without increasing bleeding, which could lead, for example, to cerebral hemorrhage.

The annexins are a family of highly homologous anti-thrombotic proteins of which ten are expressed in several human tissues (J. Benz and A. Hofmann, *Biol. Chem.* 378:177–183 (1997)). Several annexins bind calcium and negatively charged phospholipids, both of which are required for blood coagulation. Under physiological conditions, negatively charged phospholipid is mainly supplied by phosphatidylserine (PS) in activated or damaged cell membranes. In intact cells, PS is confined to the inner leaflet of the plasma membrane bilayer and is not accessible on the surface. When platelets are activated, the amounts of PS accessible on their surface, and therefore the extent of annexin binding, are greatly increased (J. Sun et al., *Thromb. Res.* 69:289–296 (1993)). In addition, microvesicles are released from the surfaces of activated platelets, greatly increasing the surface area expressing anionic phospholipids with procoagulant activity (M. Merten et al., *Circulation* 99:2577–2582 (1999); T. W. Chow et al., *J. Lab. Clin. Med.* 135:66–72 (2000)).

Proteins involved in the blood coagulation cascade (factors X, Xa, and Va) bind to membranes bearing PS on their surfaces, and to one another, forming a stable, tightly bound prothrombinase complex. Several annexins, including II, V, and VIII, bind PS with high affinity, thereby preventing the formation of a prothrombinase complex and exerting antithrombotic activity. Annexin V binds PS with very high affinity ($K_d$=1.7 nmol/L), greater than the affinity of factors X, Xa, and Va for negatively charged phospholipids (P. Thiagarajan and J. F. Tait, *J. Biol. Chem.* 265:17420–17423 (1990)). Tissue factor-dependent blood coagulation on the surface of activated or damaged endothelial cells also requires surface expression of PS, and annexin V can inhibit this process (W. L. van Heerde et al., *Arterioscler. Thromb.* 14:824–830 (1994)).

In the cellular amplification of platelet aggregation, Gas6 is released and binds to tyrosine kinase receptors on the surface of platelets. This process is associated with the completion of granule release and the formation of tight macroaggregates of platelets. Gas6 may itself be one of the adhesion molecules mediating the tight aggregation. Gas6 binds PS and can form a bridge between cells expressing complementary tyrosine kinase receptors and surfaces with available PS. Gas6 bound to Axl or another tyrosine kinase receptor expressed on platelets could therefore bind PS that is accessible on the surface of other activated platelets. Prior binding of annexin V to PS may compete with Gas6 binding, thereby suppressing Gas6-mediated platelet aggregation. If Axl and other receptors are expressed on rafts bearing PS, the inhibition of cellular amplication of platelet aggregation would be even more effective.

The binding of annexin V to activated platelets and to damaged cells probably explains the selective retention of the protein in thrombi. This has been shown in experimental animal models of venous and arterial thrombosis (J. R. Stratton et al., *Circulation* 92:3113–3121 (1995); P. Thiagarajan and C. R. Benedict, *Circulation* 96:2339–2347 (1997)), and labeled annexin has been proposed for medical imaging of vascular thrombi in humans, with reduced noise and increased safety (PCT Internatinal Publication No. WO 95/34315).

Annexins have shown anticoagulant activity in several in vitro thrombin-dependent assays, as well as in experimental animal models of venous thrombosis (J. Römisch et al., *Thromb. Res.* 61:93–104 (1991); J. Van Ryn-McKenna et al., *Thromb. Haemost.* 69:227–230 (1993)) and arterial thrombosis (Thiagarajan and Benedict, 1997). Remarkably, annexin in antithrombotic doses had no demonstrable effect on traditional ex vivo clotting tests in treated rabbits (Thiagarajan and Benedict, 1997) and did not significantly prolong bleeding times of treated rats (Van Ryn-McKenna et al., 1993). In treated rabbits annexin did not increase bleeding into a surgical incision (Thiagarajan and Benedict, 1997). Thus, annexins exert antithrombotic activity without increasing hemorrhage. Annexins do not inhibit platelet aggregation triggered by agonists other than thrombin (van Heerde et al., 1994), and platelet aggregation is the primary hemostatic mechanism.

Compositions

Annexins have a short half-life in the circulation, estimated in experimental animals to be 5 to 15 minutes (Römisch et al., 1991; Stratton et al., 1995; Thiagarajan and Benedict, 1997); annexin V also has a short half-life in the circulation of humans (H. W. Strauss et al., *J. Nucl. Med.* 41 (5 Suppl.):149P (2000)). Most of the annexin is lost into the urine, as expected of a 36 kDa protein (Thiagarajan and Benedict, 1997). In embodiments of the present invention, the effective size of an annexin molecule is increased to prevent loss from the vascular compartment into the extravascular compartment and urine, thereby prolonging its activity.

One embodiment of the present invention is a modified annexin molecule containing a recombinant human annexin protein coupled to polyethylene glycol (PEG) in such a way that the modified annexin is capable of performing the function of annexin in a phosphatidylserine (PS)-binding assay. The activity (e.g., anti-thrombotic) of the intravenously administered annexin-PEG conjugate is prolonged as compared with that of the free annexin. The recombinant annexin protein coupled to PEG can be annexin V protein or another annexin protein.

PEG consists of repeating units of ethylene oxide that terminate in hydroxyl groups on either end of a linear or, in some cases, branched chain. The size and molecular weight of the coupled PEG chain depend upon the number of ethylene oxide units it contains, which can be selected. In embodiments of present invention, any size of PEG and number of PEG chains per annexin molecule can be used such that the half-life of the modified annexin is increased, relative to annexin, while preserving the function of binding of the modified molecule to PS. Sufficient binding includes binding that is diminished from that of the unmodified annexin but is still one or more of the following: competitive with the binding of Gas6 and factors of the prothrombinase complex and therefore able to prevent thrombosis; competitive with the binding of sPLA$_2$; able to reduce adhesion among red blood cells, endothelial cells, and activated platelets; or able to exhibit any other desired activity. The optimal molecular weight of the conjugated PEG varies with the number of PEG chains. In one embodiment, two PEG molecules of molecular weight of at least about 10 kDa each are coupled to each annexin molecule. The PEG molecules can be linear or branched. The calcium-dependent binding of annexins to PS is affected not only by the size of the coupled PEG molecules, but also the sites on the protein to which PEG is bound. Optimal selection ensures that desirable properties are retained. Selection of PEG attachment sites is facilitated by knowledge of the three-dimensional structure of the molecule and by mutational and crystallographic analyses of the interaction of the molecule with phospholipid membranes (B. Campos et al., *Biochemistry* 37:8004–8010 (1998)).

In the area of drug delivery, PEG derivatives have been widely used in covalent attachment (referred to as pegylation) to proteins to enhance solubility, as well as to reduce immunogenicity, proteolysis, and kidney clearance. The superior clinical efficacy of recombinant products coupled to PEG is well established. For example, PEG-interferon alpha-2a administered once weekly is significantly more effective against hepatitis C virus than three weekly doses of the free interferon (E. J. Heathcote et al., *N. Engl. J. Med.* 343:1673–1680 (2000)). Coupling to PEG has been used to prolong the half-life of recombinant proteins in vivo (M. J. Knauf et al., *J. Biol. Chem.* 266:2796–2804 (1988)), as well as to prevent the enzymatic degradation of recombinant proteins and to decrease the immunogenicity sometimes observed with homologous products (references in Hermanson, *Bioconjugate techniques*. New York, Academic Press (1996), pp. 173–176).

In another embodiment of the invention, the modified annexin protein is a polymer of annexin proteins that has an increased effective size. It is believed that the increase in effective size results in prolonged half-life in the vascular compartment and prolonged antithrombotic and other activity. One such modified annexin is a dimer of annexin V, which has a molecular weight of, in one embodiment, approximately 64 kDa. The annexin homopolymer can be produced by bioconjugate methods or recombinant methods, and be administered by itself or in a PEG-conjugated form.

In another embodiment of the invention, recombinant annexin is expressed with, or chemically coupled to, another protein such as the Fc portion of immunoglobulin. Such expression or coupling increases the effective size of the molecule, preventing the loss of annexin from the vascular compartment and prolonging its anticoagulant and other action.

In one embodiment, a modified annexin protein of the invention is an isolated modified annexin protein. The modified annexin protein can contain annexin II, annexin V, or annexin VIII. In some embodiments, the protein is or contains modified human annexin, such as recombinant human annexin. According to the present invention, an isolated or biologically pure protein is a protein that has been removed from its natural environment. As such, "isolated" and "biologically pure" do not necessarily reflect the extent to which the protein has been purified. An isolated modified annexin protein of embodiments of the present invention can be obtained from its natural source, can be produced using recombinant DNA technology, or can be produced by chemical synthesis. As used herein, an isolated modified annexin protein can be a full-length modified protein or any homologue of such a protein. It can also be (e.g., for a pegylated protein) a modified full-length protein or a modified homologue of such a protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protein homologue of the present invention is from about 12 to about 18 nucleotides in length. There is no limit on the maximal size of such a nucleic acid molecule in that the nucleic acid molecule can include a portion of a gene, an entire gene, or multiple genes or portions thereof. Similarly, the minimal size of an annexin protein homologue or a modified annexin protein homologue of the present invention is from about 4 to about 6 amino acids in length, with preferred sizes depending on whether a full-length, multivalent (i.e., fusion protein having more than one domain, each of which has a function) protein, or functional portions of such proteins are desired. Annexin and modified annexin homologues of the present invention preferably have activity corresponding to the natural subunit, such as being able to perform the activity of the annexin protein in preventing thrombus formation.

Annexin protein and modified annexin homologues can be the result of natural allelic variation or natural mutation. The protein homologues of the present invention can also be produced using techniques known in the art, including, but not limited to, direct modifications to the protein or modifications to the gene encoding the protein using, for example, classic or recombinant DNA techniques to effect random or targeted mutagenesis.

A modified annexin protein can contain an amino acid sequence that is at least about 75%, at least about 80%, at least about 85%, at least about 90%, at least about 95%, or at least about 98% identical to amino acid sequence SEQ ID NO:3, SEQ ID NO:6, or a protein encoded by an allelic variant of a nucleic acid molecule encoding a protein containing any of these sequences. Methods to determine percent identities between amino acid sequences and between nucleic acid sequences are known to those skilled in the art. Suitable methods include computer programs such as the GCG® Wisconsin package™ (available from Accelrys Corporation), the DNAsis™ program (available from Hitachi Software, San Bruno, Calif.), the Vector NTI Suite (available from Informax, Inc., North Bethesda, Md.), or the BLAST software available on the NCBI website.

In one embodiment, a modified annexin protein includes an amino acid sequence of at least about 5 amino acids, at least about 50 amino acids, at least about 100 amino acids, at least about 200 amino acids, at least about 250 amino acids, at least about 275 amino acids, at least about 300 amino acids, or at least about 319 amino acids or the full-length annexin protein, whichever is shorter. In another embodiment, annexin proteins contain full-length proteins, i.e., proteins encoded by full-length coding regions, or post-translationally modified proteins thereof, such as mature proteins from which initiating methionine and/or signal sequences or "pro" sequences have been removed.

A fragment of a modified annexin protein of the present invention contains at least about 5 amino acids, at least about 10 amino acids, at least about 15 amino acids, at least about 20 amino acids, at least about 25 amino acids, at least about 30 amino acids, at least about 35 amino acids, at least about 40 amino acids, at least about 45 amino acids, at least about 50 amino acids, at least about 55 amino acids, at least about 60 amino acids, at least about 65 amino acids, at least about 70 amino acids, at least about 75 amino acids, at least about 80 amino acids, at least about 85 amino acids, at least about 90 amino acids, at least about 95 amino acids, or at least about 100 amino acids in length.

In one embodiment, an isolated modified annexin protein is a modified protein encoded by a nucleic acid molecule having the nucleic acid sequence SEQ ID NO:4 or by an allelic variant of a nucleic acid molecule having this sequence. Alternatively, the modified annexin protein contains a protein encoded by a nucleic acid molecule having the nucleic acid sequence SEQ ID NO:1 or by an allelic variant of a nucleic acid molecule having this sequence.

One embodiment of the present invention includes a non-native modified annexin protein encoded by a nucleic acid molecule that hybridizes under stringent hybridization conditions with an annexin gene. As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., *Molecular Cloning: A Laboratory Manual Cold Spring Harbor Labs Press* (1989), which is incorporated herein by reference. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in J. Meinkoth et al., *Anal. Biochem.* 138:267–284 (1984), which is incorporated herein by reference. In some embodiments, hybridization conditions permit isolation of nucleic acid molecules having at least about 80% nucleic acid sequence identity with the nucleic acid molecule being used to probe. In other embodiments, hybridization conditions permit isolation of nucleic acid molecules having at least about 90% nucleic acid sequence identity with the nucleic acid molecule being used to probe. In yet other embodiments, hybridization conditions permit isolation of nucleic acid molecules having at least about 95% nucleic acid sequence identity with the nucleic acid molecule being used to probe.

A modified annexin protein of one embodiment of the invention includes a protein encoded by a nucleic acid molecule that is at least about 50 nucleotides and that hybridizes under conditions that allow about 20% base pair mismatch, about 15% base pair mismatch, about 10% base pair mismatch, about 5% base pair mismatch, or about 2% base pair mismatch with a nucleic acid molecule selected from the group consisting of SEQ ID NO:1, SEQ ID NO:4, or a complement of either of these nucleic acid molecules.

As used herein, an annexin gene includes all nucleic acid sequences related to a natural annexin gene such as regulatory regions that control production of the annexin protein encoded by that gene (such as, but not limited to, transcription, translation or post-translation control regions) as well as the coding region itself. In one embodiment, an annexin gene includes the nucleic acid sequence SEQ ID NO:1. It should be noted that since nucleic acid sequencing technology is not entirely error-free, SEQ ID NO:1 (as well as other sequences presented herein), at best, represents an apparent nucleic acid sequence of the nucleic acid molecule encoding an annexin protein of the present invention.

In another embodiment, an annexin gene can be an allelic variant that includes a similar but not identical sequence to SEQ ID NO:1. An allelic variant of an annexin gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given human since the genome is diploid and/or among a population comprising two or more humans.

An isolated modified annexin protein of embodiments of the present invention can be obtained from its natural source, can be produced using recombinant DNA technology, or can be produced by chemical synthesis. As used herein, an isolated modified annexin protein can contain a full-length protein or any homologue of such a protein. Examples of annexin and modified annexin homologues include annexin and modified annexin proteins in which amino acids have been deleted (e.g., a truncated version of the protein, such as a peptide or by a protein splicing reaction when an intein has been removed or two exteins are joined), inserted, inverted, substituted and/or derivatized (e.g., by glycosylation, phosphorylation, acetylation, methylation, myristylation, prenylation, palmitoylation, amidation and/or addition of glycerophosphatidyl inositol) such that the homologue includes at least one epitope capable of eliciting an immune response against an annexin protein. That is, when the homologue is administered to an animal as an immunogen, using techniques known to those skilled in the art, the animal will produce a humoral and/or cellular immune response against at least one epitope of an annexin protein. Annexin and modified annexin homologues can also be selected by their ability to selectively bind to immune serum. Methods to measure such activities are disclosed herein. Annexin and modified annexin homologues also include those proteins that are capable of performing the function of native annexin in a functional assay; that is, are capable of binding to phosphatidylserine or to activated platelets or exhibiting antithrombotic activity. Methods for such assays are described in the Examples section and elsewhere herein.

A modified annexin protein of embodiments of the present invention may be identified by its ability to perform the function of an annexin protein subunit in a functional assay. The phrase "capable of performing the function of that subunit in a functional assay" means that the protein or modified protein has at least about 10% of the activity of the natural protein subunit in the functional assay. In other embodiments, it has at least about 20% of the activity of the natural protein subunit in the functional assay. In other embodiments, it has at least about 30% of the activity of the natural protein subunit in the functional assay. In other embodiments, it has at least about 40% of the activity of the natural protein subunit in the functional assay. In other embodiments, it has at least about 50% of the activity of the natural protein subunit in the functional assay. In other embodiments, the protein or modified protein has at least about 60% of the activity of the natural protein subunit in the functional assay. In other embodiments, the protein or modified protein has at least about 70% of the activity of the natural protein subunit in the functional assay. In other embodiments, the protein or modified protein has at least about 80% of the activity of the natural protein subunit in the functional assay. In other embodiments, the protein or modified protein has at least about 90% of the activity of the natural protein subunit in the functional assay. Examples of functional assays are described herein.

An isolated protein of the present invention can be produced in a variety of ways, including recovering such a protein from a bacterium and producing such a protein recombinantly. One embodiment of the present invention is a method to produce an isolated modified annexin protein of the present invention using recombinant DNA technology. Such a method includes the steps of (a) culturing a recombinant cell containing a nucleic acid molecule encoding a modified annexin protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques.

Isolated proteins of the present invention can be retrieved in "substantially pure" form. As used herein, "substantially pure" refers to a purity that allows for the effective use of the protein in a functional assay.

Modified Annexin Nucleic Acid Molecules or Genes

Another embodiment of the present invention is an isolated nucleic acid molecule capable of hybridizing under stringent conditions with a gene encoding a modified annexin protein such as a homodimer of annexin V. Such a nucleic acid molecule is also referred to herein as a modified annexin nucleic acid molecule. On embodiment is an isolated nucleic acid molecule that hybridizes under stringent conditions with a modified annexin gene. The characteristics of such genes are disclosed herein. In accordance with embodiments of the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a modified annexin gene includes all nucleic acid sequences related to a natural annexin gene, such as regulatory regions that control production of an annexin protein encoded by that gene (such as, but not limited to, transcriptional, translational, or post-translational control regions) as well as the coding region itself. A nucleic acid molecule of the present invention can be an isolated modified annexin nucleic acid molecule or a homologue thereof. A nucleic acid molecule of the present invention can include one or more regulatory regions, full-length or partial coding regions, or combinations thereof. The minimal size of a modified annexin nucleic acid molecule of the present invention is the minimal size capable of forming a stable hybrid under stringent hybridization conditions with a corresponding natural gene. Annexin nucleic acid molecules can also include a nucleic acid molecule encoding a hybrid protein, a fusion protein, a multivalent protein or a truncation fragment.

An isolated nucleic acid molecule of embodiments of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning, etc.) or chemical synthesis. Isolated modified annexin nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the ability of the nucleic acid molecule to encode an annexin protein of the present invention or to form stable hybrids under stringent conditions with natural nucleic acid molecule isolates.

A modified annexin nucleic acid molecule homologue can be produced using a number of methods known to those skilled in the art (see, e.g., Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures, and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against an annexin protein and/or to function in a clotting assay, or other functional assay), and/or by hybridization with isolated annexin-encoding nucleic acids under stringent conditions.

An isolated modified annexin nucleic acid molecule of embodiments of the present invention can include a nucleic acid sequence that encodes at least one modified annexin protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a modified annexin protein.

One embodiment of the present invention is a modified annexin nucleic acid molecule that is capable of hybridizing under stringent conditions to a nucleic acid strand that encodes at least a portion of a modified annexin protein or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. One embodiment of the present invention is a modified annexin nucleic acid molecule that includes a nucleic acid sequence having at least about 65 percent, at least about 70 percent, at least about 75 percent, at least about 80 percent, at least about 85 percent, at least about 90 percent, or at least about 95 percent homology with the corresponding region(s) of the nucleic acid sequence encoding at least a portion of a modified annexin protein. One embodiment is a modified annexin nucleic acid molecule capable of encoding a homodimer of an annexin protein or homologue thereof.

Annexin nucleic acid molecules include SEQ ID NO:4 and an allelic variants of SEQ ID NO:4.

Knowing a nucleic acid molecule of a modified annexin protein of embodiments of the present invention allows one skilled in the art to make copies of that nucleic acid molecule as well as to obtain a nucleic acid molecule including additional portions of annexin protein-encoding genes (e.g., nucleic acid molecules that include the translation start site and/or transcription and/or translation control regions), and/or annexin nucleic acid molecule homologues. Knowing a portion of an amino acid sequence of an annexin protein of the present invention allows one skilled in the art to clone nucleic acid sequences encoding such an annexin protein. In addition, a desired modified annexin nucleic acid molecule can be obtained in a variety of ways including screening appropriate expression libraries with antibodies that bind to annexin proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used).

Embodiments of present invention also include nucleic acid molecules that are oligonucleotides capable of hybridizing, under stringent conditions, with complementary regions of other, potentially longer, nucleic acid molecules of the present invention that encode at least a portion of a modified annexin protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules, or in therapeutic applications to modulate modified annexin production. Such therapeutic applications include the use of such oligonucleotides in, for example, antisense-, triplex formation-, ribozyme- and/or RNA drug-based technologies. The present invention, therefore, includes such oligonucleotides and methods to modulate the production of modified annexin proteins by use of one or more of such technologies.

Natural, Wild-Type Bacterial Cells and Recombinant Molecules and Cells

Embodiments of the present invention also include a recombinant vector, which includes a modified annexin nucleic acid molecule of the present invention inserted into any vector capable of delivering the nucleic acid molecule into a host cell. Such a vector contains heterologous nucleic acid sequences, that is, nucleic acid sequences that are not naturally found adjacent to modified annexin nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of modified annexin nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a modified annexin subunit protein of the present invention by culturing a cell capable of expressing the protein under conditions effective to produce the protein, and recovering the protein. In an alternative embodiment, the method includes producing an annexin protein by culturing a cell capable of expressing the protein under conditions effective to produce the annexin protein, recovering the protein, and modifying the protein by coupling it to an agent that increases its effective size.

In one embodiment, the cell to culture is a natural bacterial cell, and modified annexin is isolated from these cells. In another embodiment, the cell to culture is a recombinant cell that is capable of expressing the modified annexin protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable nucleic acid molecules with which to transform a host cell are disclosed herein.

Suitable host cells to transform include any cell that can be transformed and that can express the introduced modified annexin protein. Such cells are, therefore, capable of producing modified annexin proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal, and plant cells. For example, host cells can include bacterial cell such as E. coli cells. Alternative host cells are untransformed (wild-type) bacterial cells producing cognate modified annexin proteins, including attenuated strains with reduced pathogenicity, as appropriate.

A recombinant cell can be produced by transforming a host cell with one or more recombinant molecules, each containing one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. The expression vector may also be capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence that is capable of controlling the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to the art. Suitable transcription control sequences include those which function in bacterial, yeast, insect and mammalian cells, such as, but not limited to, tac, lac, tzp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, *Rous sarcoma* virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an annexin protein. A preferred transcription control sequence is the Kozak strong promotor and initiation sequence.

Expression vectors of embodiments of the present invention may also contain secretory signals (i.e., signal segment nucleic acid sequences) to enable an expressed annexin protein to be secreted from the cell that produces the protein. Suitable signal segments include an annexin protein signal segment or any heterologous signal segment capable of directing the secretion of an annexin protein, including fusion proteins, of the present invention. Signal segments include, but are not limited to, tissue plasminogen activator (t-PA), interferon, interleukin, growth hormone, histocompatibility and viral envelope glycoprotein signal segments.

Expression vectors of embodiments of the present invention may also contain fusion sequences which lead to the expression of inserted nucleic acid molecules of the present invention as fusion proteins. Inclusion of a fusion sequence as part of a modified annexin nucleic acid molecule of the present invention can enhance the stability during production, storage and/or use of the protein encoded by the nucleic acid molecule. Furthermore, a fusion segment can function as a tool to simplify purification of a modified annexin protein, such as to enable purification of the resultant fusion protein using affinity chromatography. One fusion segment that can be used for protein purification is the 8-amino acid peptide sequence asp-tyr-lys-asp-asp-asp-asp-lys (SEQ ID NO:9).

A suitable fusion segment can be a domain of any size that has the desired function (e.g., increased stability and/or purification tool). It is within the scope of the present invention to use one or more fusion segments. Fusion segments can be joined to amino and/or carboxyl termini of an annexin protein. Another type of preferred fusion protein is a fusion protein wherein the fusion segment connects two or more annexin proteins or modified annexin proteins. Linkages between fusion segments and annexin proteins can be constructed to be susceptible to cleavage to enable straightforward recovery of the annexin or modified annexin proteins. Fusion proteins are preferably produced by culturing a recombinant cell transformed with a fusion nucleic acid sequence that encodes a protein including the fusion segment attached to either the carboxyl and/or amino terminal end of an annexin protein.

A recombinant molecule of the present invention is a molecule that can include at least one of any nucleic acid molecule heretofore described operatively linked to at least one of any transcription control sequence capable of effectively regulating expression of the nucleic acid molecules in the cell to be transformed. A suitable recombinant molecule includes one or more nucleic acid molecules of the present invention, with those that encode one or more modified annexin proteins being particularly preferred. Recombinant molecules of embodiments of the present invention and their production are described in the Examples section. Similarly, a recombinant cell includes one or more nucleic acid molecules of the present invention, with those that encode one or more annexin proteins. Recombinant cells of embodiments of the present invention include those disclosed in the Examples section.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce annexin or modified annexin proteins of the present invention by culturing such cells under conditions effective to produce such a protein, and recovering the protein. Effective conditions to produce a protein include, but are -not limited to, appropriate media, bioreactor, temperature, pH and oxygen conditions that permit protein production. An appropriate, or effective, medium refers to any medium in which a cell of the present invention, when cultured, is capable of producing an annexin or modified annexin protein. Such a medium is typically an aqueous medium comprising assimilable carbohydrate, nitrogen and phosphate sources, as well as appropriate salts, minerals, metals and other nutrients, such as vitamins. The medium may comprise complex, nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant annexin proteins may either remain within the recombinant cell; be secreted into the fermentation medium; be secreted into a space between two cellular membranes, such as the periplasmic space in *E. coli*; or be retained on the outer surface of a cell or viral membrane. Methods to purify such proteins are disclosed in the Examples section.

Antibodies

The present invention also includes isolated anti-modified annexin antibodies and their use. An anti-modified annexin antibody is an antibody capable of selectively binding to a modified annexin protein. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protein against which the antibody was raised (i.e., to be able to distinguish that protein from unrelated components in a mixture). Binding affinities, commonly expressed as equilibrium association constants, typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, e.g., Sambrook et al., 1989.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a modified annexin nucleic acid molecule of the present invention.

Anti-modified annexin antibodies of the present invention include antibodies raised in an animal administered a modified annexin. Anti-modified annexin antibodies of the present invention also include antibodies raised in an animal against one or more modified annexin proteins of the present invention that are then recovered from the cell using techniques known to those skilled in the art. Yet additional antibodies of the present invention are produced recombinantly using techniques as heretofore disclosed for modified annexin proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-modified annexin antibodies of the present invention have a variety of uses that are within the scope of the present invention. Anti-modified annexin antibodies can be used as tools to screen expression libraries and/or to recover desired proteins of the present invention from a mixture of proteins and other contaminants.

A preferred anti-modified annexin antibody of the present invention can selectively bind to a modified annexin protein.

Gene Therapy

In a further embodiment, the therapeutic agents of the present invention are useful for gene therapy. As used herein, the phrase "gene therapy" refers to the transfer of genetic material (e.g., DNA or RNA) of interest into a host to treat or prevent a genetic or acquired disease or condition. The genetic material of interest encodes a product (e.g., a protein polypeptide, peptide or functional RNA) whose production in vivo is desired. For example, the genetic material of interest can encode a hormone, receptor, enzyme or (poly) peptide of therapeutic value. In a specific embodiment, the subject invention utilizes a class of lipid molecules for use in non-viral gene therapy which can complex with nucleic acids as described in Hughes et al., U.S. Pat. No. 6,169,078, incorporated herein by reference, in which a disulfide linker is provided between a polar head group and a lipophilic tail group of a lipid.

These therapeutic compounds of the present invention effectively complex with DNA and facilitate the transfer of DNA through a cell membrane into the intracellular space of a cell to be transformed with heterologous DNA. Furthermore, these lipid molecules facilitate the release of heterologous DNA in the cell cytoplasm thereby increasing gene transfection during gene therapy in a human or animal.

Cationic lipid-polyanionic macromolecule aggregates may be formed by a variety of methods known in the art. Representative methods are disclosed by Felgner et al., Proc. Natl. Acad. Sci. USA 86: 7413–7417 (1987); Eppstein et al., U.S. Pat. No. 4,897,355; Behr et al., Proc. Natl. Acad. Sci. USA 86:6982–6986 (1989); Bangham et al., J. Mol. Biol. 23:238–252 (1965); Olson et al., Biochim. Biophys. Acta 557:9 (1979); Szoka, et al., Proc. Natl. Acad. Sci. 75:4194 (1978); Mayhew et al., Biochim. Biophys. Acta 775:169 (1984); Kim et al., Biochim. Biophys. Acta 728:339 (1983); and Fukunaga et al., Endocrinol. 115:757 (1984), all incorporated herein by reference. In general, aggregates may be formed by preparing lipid particles consisting of either (1) a cationic lipid or (2) a cationic lipid mixed with a colipid, followed by adding a polyanionic macromolecule to the lipid particles at about room temperature (about 18 to 26° C.). In general, conditions are chosen that are not conducive to deprotection of protected groups. In one embodiment, the mixture is then allowed to form an aggregate over a period of about 10 minutes to about 20 hours, with about 15 to 60 minutes most conveniently used. Other time periods may be appropriate for specific lipid types. The complexes may be formed over a longer period, but additional enhancement of transfection efficiency will not usually be gained by a longer period of complexing.

The compounds and methods of the subject invention can be used to intracellularly deliver a desired molecule, such as, for example, a polynucleotide, to a target cell. The desired polynucleotide can be composed of DNA or RNA or analogs thereof. The desired polynucleotides delivered using the present invention can be composed of nucleotide sequences that provide different functions or activities, such as nucleotides that have a regulatory function, e.g., promoter sequences, or that encode a polypeptide. The desired polynucleotide can also provide nucleotide sequences that are antisense to other nucleotide sequences in the cell. For example, the desired polynucleotide when transcribed in the cell can provide a polynucleotide that has a sequence that is antisense to other nucleotide sequences in the cell. The antisense sequences can hybridize to the sense strand sequences in the cell. Polynucleotides that provide antisense sequences can be readily prepared by the ordinarily skilled artisan. The desired polynucleotide delivered into the cell can also comprise a nucleotide sequence that is capable of forming a triplex complex with double-stranded DNA in the cell.

Therapeutic Methods

A pharmaceutical composition containing a therapeutically effective amount any of the above-described modified annexin proteins is administered to treat sickle-cell disease (homozygous or heterozygous) or related disorders, including vaso-occlusive crises, pain crises, Acute Chest Sydrome (ACS), and any other symptom or disorder related to sickle-cell disease. Generally, the composition used is administered to an animal in an effective amount. Generally, a therapeutically effective amount is an amount effective either (1) to reduce the symptoms of the disease sought to be treated or (2) to induce a pharmacological change relevant to treating the disease sought to be treated.

An effective amount includes an amount effective to exert prolonged activity without substantially increasing the risk of hemorrhage. In treating sickle-cell disease, activity includes at least one of: inhibiting activity of $sPLA_2$ on surface-exposed PS, decreasing adhesion of red blood cells to endothelial cells, decreasing platelet aggregation, decreasing adhesion of platelets to red blood cells and endothelial cells, decreasing pain, decreasing the severity of vaso-occlusive crises, decreasing the severity of ACS, and decreasing the severity of any symptoms associated with sickle-cell disease. As used herein, prolonged activity refers to the time of activity of the modified annexin protein with respect to the time of activity of the same amount (molar) of an unmodified annexin protein. Activity can be prolonged by at least a factor of about two, at least a factor of about five, or at least a factor of about ten. Preferably, the effective amount does not substantially increase the risk of hemorrhage compared with the hemorrhage risk of the same subject to whom the modified annexin has not been administered. Preferably, the hemorrhage risk is very small and, at most, below that provided by alternative treatments available in the prior art. A therapeutically effective amount of the composition can be any amount or dose sufficient to bring about the desired effect and depends, in part, on the condition, type, and severity of the disease, the size and condition of the patient, as well as other factors known to those skilled in the art. The dosages can be given as a single dose, or as several doses, for example, divided over the course of several weeks.

The modified annexin can be administered intravenously or as a bolus or infusion in the dosage range of about 1 to about 100 mg. A preferred time of administration is early in the course of a sickle-cell crisis, when the modified annexin is expected to alleviate the symptoms associated with the crises. If serum $PLA_2$ elevation or other biomarker suggests that the patient is likely to develop ACS, administration of modified annexin may prevent that dangerous complication. If a patient with sickle-cell disease develops a systemic bacterial infection, administration of a modified annexin may prevent complications. If a patient with sickle-cell disease develops a cerebral thrombosis, administration of a modified annexin may prevent extension or recurrence of the thrombosis without increasing the risk of cerebral hemorrhage. Other times when administration of a modified annexin will benefit patients with sickle-cell disease will be apparent to physicians experienced in handling the many complications of that disorder.

In an additional embodiment, the present invention provides a method of screening for a modified annexin protein that inhibits $sPLA_2$ activity on red blood cells or microvesicles, by contacting PS-exposing red blood cells with at least one test modified annexin protein in the presence of $sPLA_2$ and comparing the hydrolytic activity of $sPLA_2$ in the presence and absence of the test modified annexin protein. A decrease in hemolysis in the presence of the test modified annexin protein is indicative of a modified annexin protein that inhibits $sPLA_2$ activity. Additionally, the time over which activity is sustained in the presence of the test modified annexin protein can be compared with a time of activity in the presence of unmodified annexin to determine the prolongation of activity associated with the test modified annexin protein. Also included within the scope of the present invention are modified annexin proteins that inhibit $sPLA_2$ activity as identified by this method.

All of the references cited herein are incorporated herein by reference.

The following examples further illustrate embodiments of the invention without limiting the embodiments to the details disclosed.

EXAMPLES

Example 1
Preparation of Annexin V Homodimer by Chemical Cross-linking

Bioconjugate methods can be used to produce homopolymers or heteropolymers of annexin; methods are reviewed by Hermanson, 1996. Dimers can be made by chemically cross-linking two annexin molecules using methods known in the art.

In one approach to chemical cross-linking of two annexin V molecules, a homobifunctional cross-linking reagent targeting the amine group of lysine residues is employed. EDC (1-ethyl-3-(3-dimethylaminopropyl)-carbodiimide hydrochloride) can be used to form active ester groups with carboxylate groups using sulfo-NHS (N-hydroxysulfosuccinamide). This increases the stability of the active intermediate, which reacts with an amine to give a stable amide linkage. The conjugation can be carried out as described in Hermanson, 1996. Alternatively, the carboxyl termini can be targeted.

In general, a wide variety of bifunctional cross-linking reagents, including specific homobifunctional reagents with different spacer arms, are available commercially. Alternatively, custom reagents can be synthesized. It is preferable to select concentrations of annexin and cross-linker that optimize dimer formation while minimizing the number of different dimer forms that are produced. These concentrations depend on the particular cross-linker employed. Depending upon product purity, purification may be desired. For example, chromatographic purification can be performed by size exclusion chromatography followed by anion exchange chromatography.

Comparison of the sequence of different annexins and the crystal structure of human annexin V suggests that the N-termini are not conserved and that cross-linking via the N-termini may allow retention of PS binding. The PS/$Ca^{2+}$ binding domain is on one face of the annexin V molecule. The cross-linking reaction can be carried out in the presence of PS liposomes and $Ca^{2+}$ to protect the PS binding domain during cross-linking. Conditions can be chosen to select for primary amines on the protein. Alternatively, a cysteine-reactive cross-linking agent, which binds to the single cysteine residue located near the C-terminus of annexin V, may be employed.

Example 2
Preparation of Recombinant Annexin V Homodimer

Annexins can be purified from human tissues or produced by recombinant technology. For instance, annexin V can be purified from human placentas as described by Funakoshi et al. (1987). Examples of recombinant products are the expression of annexin II and annexin V in *Escherichia coli* (H. -M. Kang et al., *Trends Cardiovasc. Med.* 9:92–102 (1999); Thiagarajan and Benedict, 1997, 2000). A rapid and efficient purification method for recombinant annexin V, based on $Ca^{2+}$-enhanced binding to phosphatidylserine-containing liposomes and subsequent elution by EDTA, has been described by A. Burger et al., *FEBS Lett.* 329:25–28 (1993). This procedure can be improved by the use of phosphatidylserine coupled to a solid phase support.

Recombinant methods can also be used to produce fusion proteins, e.g., annexin expressed with the Fc portion of immunoglobulin or another protein. The heterotetramer of annexin II with P11 has also been produced in *E. coli* (Kang et al., 1999). All of these procedures increase the molecular weight of annexin and have the potential to increase the half-life of annexin in the circulation and prolong its anti-coagulant effect.

A homodimer of annexin V can be produced using a DNA construct shown schematically in FIG. 1 (5'-3' sense strand) (SEQ ID NO:4) and coding for an amino acid sequence represented by SEQ ID NO:6. In this example, the annexin V gene is cloned into the expression vector pCMV FLAG 2 (available from Sigma-Aldrich) at EcoRI and BglII sites. The exact sequences prior to and after the annexin V sequence are unknown and denoted as "x". It is therefore necessary to sequence the construct prior to modification to assure proper codon alignment. The pCMV FLAG 2 vector comes with a strong promotor and initiation sequence (Kozak) and start site (ATG) built in. The start codon before each annexin V gene must therefore be removed, and a strong stop for tight expression should be added at the terminus of the second annexin V gene. The vector also comes with an 8-amino acid peptide sequence that can be used for protein purification (asp-tyr-lys-asp-asp-asp-asp-lys) (SEQ ID NO:9). Alternatively, a His tag can be placed at the N-terminal end of the dimer to facilitate purification. A 14-amino acid spacer with glycine-serine swivel ends allows optimal rotation between tandem genes. Addition of restriction sites PvuII and ScaI allow removal of the linker if necessary. The linker sequence may provide flexibility so that domains of both annexin monomers can interact with PS. Addition of a protease site allows cleavage of tandem proteins following expression. PreScission™ protease is available from Amersham Pharmacia Biotech and can be used to cleave tandem proteins.

Human Annexin V has the following amino acid sequence:

(SEQ ID NO:3)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD

The nucleotide sequence of human annexin V, inserted as indicated in the DNA construct illustrated in FIG. 1, is as follows:

(SEQ ID NO:1)
GCACAGGTTCTCAGAGGCACTGTGACTGACTTCCCTGGATTTGATGAGCG

GGCTGATGCAGAAACTCTTCGGAAGGCTATGAAAGGCTTGGGCACAGATG

AGGAGAGCATCCTGACTCTGTTGACATCCCGAAGTAATGCTCAGCGCCAG

GAAATCTCTGCAGCTTTTAAGACTCTGTTTGGCAGGGATCTTCTGGATGA

CCTGAAATCAGAACTAACTGGAAAATTTGAAAAATTAATTGTGGCTCTGA

TGAAACCCTCTCGGCTTTATGATGCTTATGAACTGAAACATGCCTTGAAG

GGAGCTGGAACAAATGAAAAAGTACTGACAGAAATTATTGCTTCAAGGAC

ACCTGAAGAACTGAGAGCCATCAAACAAGTTTATGAAGAAGAATATGGCT

CAAGCCTGGAAGATGACGTGGTGGGGACACTTCAGGGTACTACCAGCGG

ATGTTGGTGGTTCTCCTTCAGGCTAACAGAGACCCTGATGCTGGAATTGA

TGAAGCTCAAGTTGAACAAGATGCTCAGGCTTTATTTCAGGCTGGAGAAC

TTAAATGGGGACAGATGAAGAAAAGTTTATCACCATCTTTGGAACACGA

AGTGTGTCTCATTTGAGAAAGGTGTTTGACAAGTACATGACTATATCAGG

ATTTCAAATTGAGGAAACCATTGACCGCGAGACTTCTGGCAATTTAGAGC

AACTACTCCTTGCTGTTGTGAAATCTATTCGAAGTATACCTGCCTACCTT

GCAGAGACCCTCTATTATGCTATGAAGGGAGCTGGGACAGATGATCATAC

CCTCATCAGAGTCATGGTTTCCAGGAGTGAGATTGATCTGTTTAACATCA

GGAAGGAGTTTAGGAAGAATTTTGCCACCTCTCTTTATTCCATGATTAAG

GGAGATACATCTGGGGACTATAAGAAAGCTCTTCTGCTGCTCTGTGGAGA

AGATGAC

Example 3
In Vitro and In Vivo Antithrombotic Assays

In vitro assays determine the ability of modified annexin proteins to bind to activated platelets. Annexin V binds to platelets, and this binding is markedly increased in vitro by activation of the platelets with thrombin (Thiagarajan and Tait, 1990; Sun et al., 1993). The modified annexin proteins of the present invention are prepared in such a way that they perform the function of annexin, i.e., bind to platelets and prevent protein S from binding to platelets (Sun et al., 1993). The modified annexin proteins also perform the function of exhibiting the same anticoagulant activity in vitro that unmodified annexin proteins exhibit.

Binding of modified annexin to PS on liposomes can be assayed through a competitive reaction between the modified annexin and fluorescein-labeled annexin V (J. F. Tait et al., *J. Biol. Chem.* 264:7944–7949 (1989)). Annexin V conjugated with fluorescein 5-isothiocyanate has anticoagulant activity comparable to that of the unlabeled annexin V and exhibits $Ca^{2+}$-dependent binding to liposomes, which can be detected by fluorescence quenching. Fluorescent annexin V binds to liposomes composed of 80% phosphatidylcholine and 20% PS with high affinity ($K_d$=1.2 nM). Binding is specific. Fluorescent annexin V binds very weakly ($K_d$>20000 nM) to neutral or anionic phospholipid monomers; such binding is $Ca^{2+}$-independent. This method may be used as a competitive assay to determine the affinity (relative to unmodified annexin) of different modified annexins for PS, allowing monitoring of the effects of cross-linking conditions and linkers of various lengths.

Methods for measuring the clotting time include the prothrombin time (PT), for extrinsic coagulation, and the activated partial thromboplastin time (APTT), for intrinsic coagulation (Fritsma, in *Hemostasis and thrombosis in the clinical laboratory* (Corriveau, D. M. and Fritsma, G. A., eds) J. P. Lipincott Co., Philadelphia (1989), pp. 92–124). PT is measured by incubating human plasma with various forms of annexin V and modified annexin V before adding $CaCl_2$ to initiate clotting. Clotting is monitored optically. APTT is measured similarly, with the addition of a PTT reagent incubated with the plasma and annexin before clotting is initiated.

Figure 2:
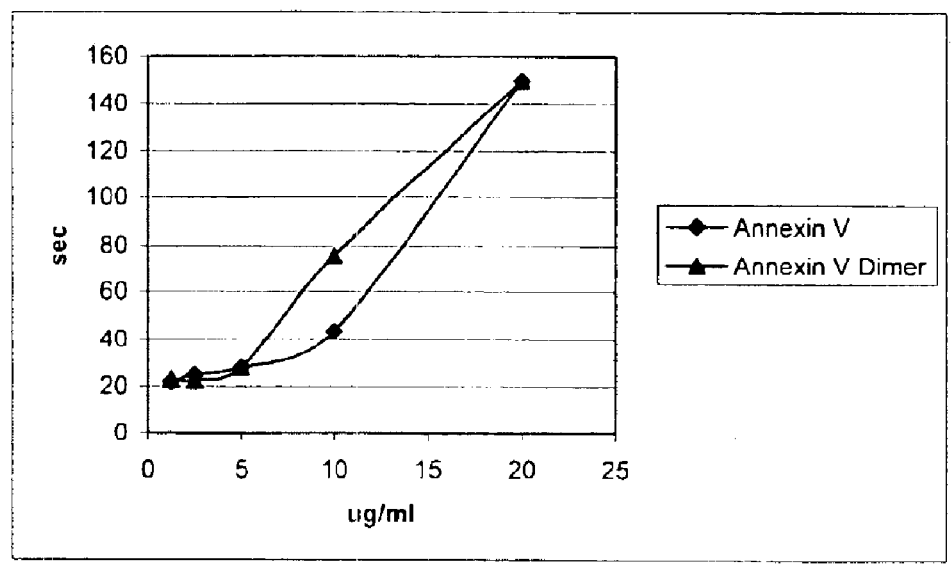
FIG. 2 is a plot of clotting time in a prothrombin time assay comparing the anticoagulant potency of recombinant human annexin V and the annexin V homodimer.

FIG. 2 is a plot of clotting time versus amount of recombinant human annexin V and recombinant human annexin V homodimer as measured by the prothrombin time assay. The annexin homodimer was prepared as described above. As shown, the homodimer has approximately equal anticoagulant activity to that of the annexin monomer. Additionally, the homodimer did not itself cause platelet aggregation.

In vivo assays determine the antithrombotic activity of annexin proteins. Annexin V has been shown to decrease venous thrombosis induced by a laser or photochemically in rats (Römisch et al., 1991). The maximal anticoagulant effect was observed between 15 and 30 minutes after intravenous administration of annexin V, as determined functionally by thromboelastography. The modified annexin proteins of the present invention preferably show prolonged activity in such a model relative to that of unmodified annexin. Annexin V was also found to decrease fibrin accretion in a rabbit model of jugular vein thrombosis (Van Ryn-McKenna et al., 1993). Air injection was used to remove the endothelium, and annexin V was shown to bind to the treated vein but not to the control contralateral vein. Decreased fibrin accumulation in the injured vein was not associated with systemic anticoagulation. Heparin did not inhibit fibrin accumulation in the injured vein. The modified annexin proteins of the present invention preferably perform the function of annexin in this model of venous thrombosis. A rabbit model of arterial thrombosis was used by Thiagarajan and Benedict, 1997. A partially occlusive thrombus was formed in the left carotid artery by application of an electric current. Annexin V infusion strongly inhibited thrombosis as manifested by measurements of blood flow, thrombus weight, labeled fibrin deposition and labeled platelet accumulation. A rat model similar to that of Römisch et al. (1991) can be used to show the in vivo anticoagulant effect of modified annexins and their duration.

Example 4
Conjugation of PEG to Annexin V

Annexins can be coupled to polyethylene glycol (PEG) by any of several well-established procedures (reviewed by Hermanson, 1996) in a process referred to as pegylation. The present invention includes chemically-derivatized annexin molecules having mono- or poly-(e.g., 2–4) PEG moieties. Methods for preparing a pegylated annexin generally include the steps of (a) reacting the annexin with polyethylene glycol (such as a reactive ester or aldehyde derivative of PEG) under conditions whereby the annexin becomes attached to one or more PEG groups and (b) obtaining the reaction product or products. In general, the optimal reaction conditions for the reactions must be determined case by case based on known parameters and the desired result. Furthermore, the reaction may produce different products having a different number of PEG chains, and further purification may be needed to obtain the desired product.

Conjugation of PEG to annexin V can be performed using the EDC plus sulfo-NHS procedure. EDC (1-ethyl-3-(3-dimethylaminopropyl)-carbodiimide hydrochloride) is used to form active ester groups with carboxylate groups using sulfo-NHS (N-hydroxysulfosuccinamide). This increases the stability of the active intermediate, which reacts with an amine to give a stable amide linkage. The conjugation can be carried out as described in Hermanson, 1996.

Recombinant human annexin V was produced in *E. coli* as described in Thiagarajan and Benedict (1997) and Burger et al. (1993) and pegylated using the method of Hermanson, 1996, as described above. Both 10-kDa and 20-kDa PEG were attached to the annexin. The PEG chains had one end capped and the other end bearing an active NHS ester. As described in F. M. Veronese et al., *Biomaterials* 22:405 (2001), this form of PEG forms covalent bonds with lysine residues, many of which are located on the side of annexin V not participating in PS binding. Conditions were chosen such that a mean of two moles of 20-kDa PEG were coupled to each mole of annexin.

Conjugation protocols employed a buffer exchange of the protein into a solution of 10 mM PBS and 15 mM NaCl. This provides the optimal pH and buffer conditions for the conjugations, as well as removes azide and other preservatives that may interfere with the reaction. The protein and PEG were mixed together at fixed molar ratios and incubated for one hour at room temperature. At the end of the hour, 1 M glycine was added to a final concentration of 50 mM and mixed with the conjugate for 20 minutes to cap any non-reacted PEG.

Example 5
Purification of Pegylated Annexin V

Pegylated annexin V was purified by size-exclusion chromatography to separate unreacted protein and PEG. Separation was performed using a VISION™ Workstation (Applied Biosystems) with an AFC 2000 autosampler using a 10/30-superdex G-200 FPLC column from Pharmacia, equilibrated in 10 mM HEPES buffer with 15 mM NaCl. This buffer is compatible with the 5 mM $Ca^{2+}$ required for subsequent activity assays. The flow rate was set at 0.5 ml/min. The system was calibrated with standards to allow assignation of approximate molecular size based on retention time.

Figure 3:
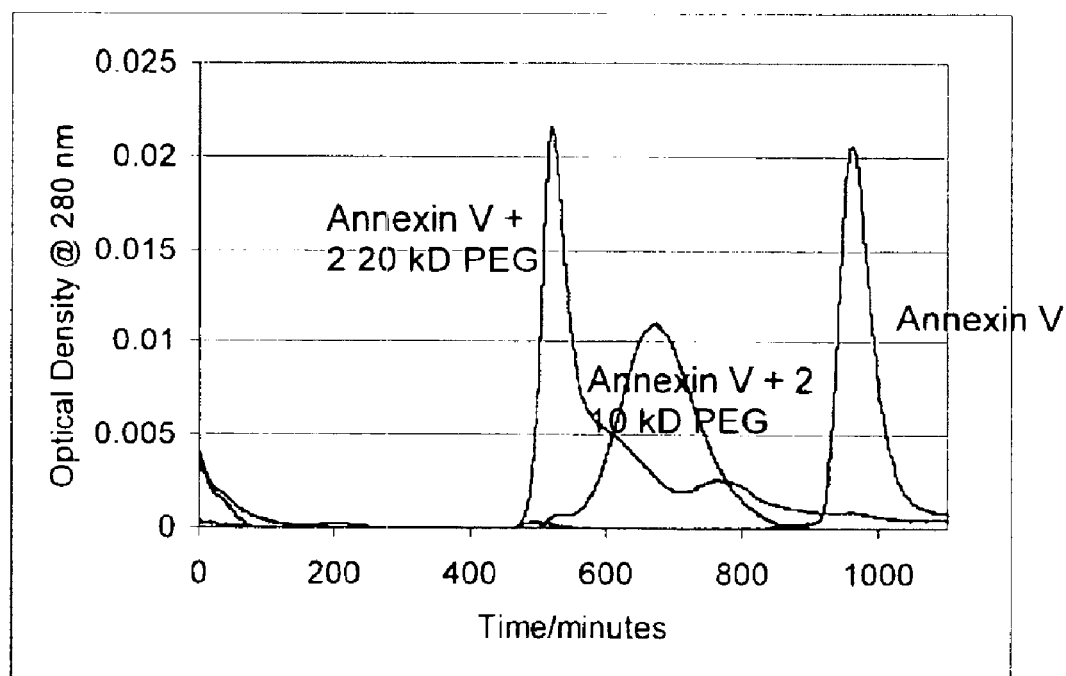
FIG. 3 is a plot of optical density versus retention time for a size-exclusion chromatographic separation of pegylated annexin and unreacted annexin.

FIG. 3 is a plot of optical density at 280 nm versus elution time for annexin V, annexin V pegylated with 2 10-kD PEG chains, and annexin V pegylated with 2 20-kD PEG chains. Based on the retention time standards, it can be determined that the conjugation of 2 moles of 20-kD PEG to one mole of annexin V gave a product with a molecular weight close to the expected value of 76 kDa.

Additional purification can be performed by ion-exchange and reverse-phase chromatography, in whichever order optimizes separation. Following separation by gel filtration, purification of the pegylated annexin can be performed by adsorption to liposomes in the presence of $Ca^{2+}$. Elution from the liposomes is accomplished by addition of EDTA. Such adsorption selects for pegylated forms that retain the desired $Ca^{2+}$-dependent PS binding.

Example 6
Anticoagulant Activity of Pegylated Annexin

The anticoagulant activity of pegylated annexin was investigated in prothrombin time (PTT) and activated prothrombin time (aPTT) measurements. PTT was measured by incubating human plasma with annexin, pegylated annexin, and dimerized annexin before adding $CaCl_2$ to initiate clotting, which is monitored optically. The aPTT is quantified similarly, except that an aPTT reagent is preincubated with the plasma before $CaCl_2$ is added to initiate clotting.

Figure 4:
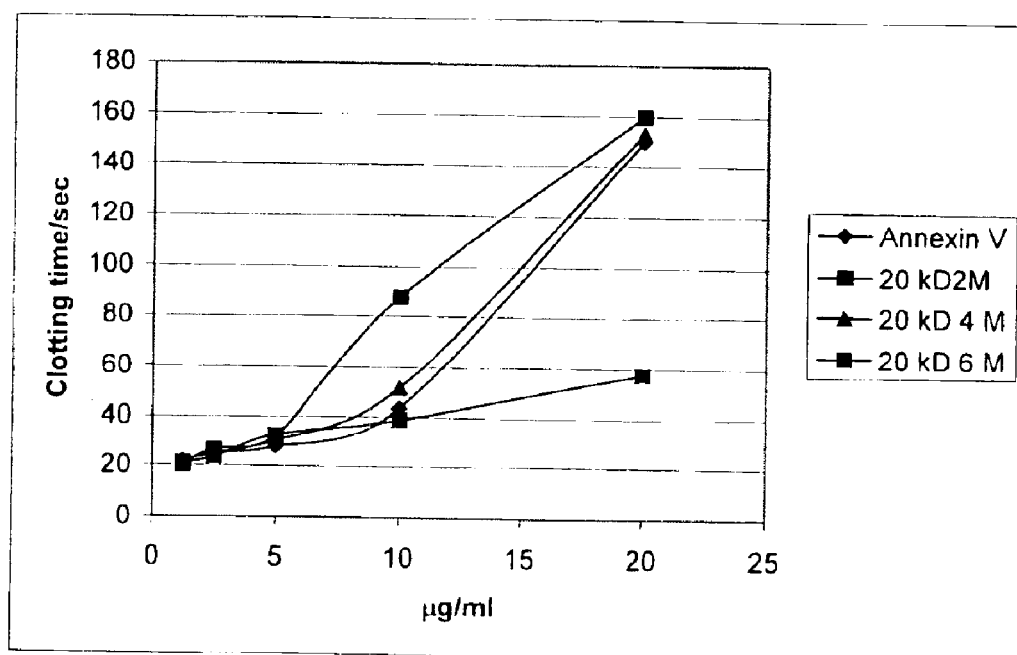
FIG. 4 is a plot of clotting time in a prothrombin time assay comparing the anticoagulant potency of recombinant human annexin V and various forms of pegylated recombinant human annexin V.

Results are shown in FIG. 4, a plot of clotting time versus amount of annexin added. As shown, the pegylated annexin containing 2 moles of PEG was more active than annexin itself. Conjugating 2 moles of PEG to one mole of annexin was superior to conjugating 4 moles, and 6 moles was not tolerated. The 10-kDa PEG conjugate (not shown) was also active, although somewhat less than the 20-kD conjugate.

These results illustrate that pegylated annexin retains its PS-binding and antithrombotic activity.

Example 7
Measuring Half-life of Modified and Unmodified Annexin V

The half-life of annexin in rabbits can be assessed as described in P. Thiagarajan et al., *Circulation* 96:2339–2347 (1997). In this method, radiolabeled annexin is injected into rabbits and its concentration in serum monitored. Purified annexin is labeled with $^{125}I$ using $^{125}I$-NaI by the Iodo-Gen method to a specific activity of 350 cmp/ng. Venous blood samples are collected at varying times after intravenous injection and residual $^{125}I$-annexin quantified. For monomeric annexin, approximately 90% is cleared within 5 minutes, primarily through renal clearance. The same procedure can be repeated for modified annexin. The half-life of modified annexin is expected to be much longer.

Example 8
In Vitro $sPLA_2$ Hydrolysis Assays

Assays can be performed to determine the inhibitory effects of modified annexins on the activity of $sPLA_2$. Binding of modified annexins to PS on the surface of red blood cells inhibits $sPLA_2$ hydrolysis of PS. The latter generates products leading to lysis of red blood cells and liberation of hemoglobin (hemolysis). PS-exposing red blood cells are incubated with modified annexin before $sPLA_2$ is added to the cells. At different time points following $sPLA_2$ addition, the amount of free hemoglobin is measured as an indication of the extent of PS hydrolysis. For example, one $\mu l$ of red blood cells, approximately $10^7$ cells, is added to each of a number of test tubes. The total amount of PS in each such tube is approximately 0.5 nmol. At varying time points after the addition of $sPLA_2$, the extent of hemolysis is measured. Cells incubated with annexin or modified annexins are expected to exhibit much lower PS hydrolysis. This procedure can be repeated with different amounts and forms of modified annexin being incubated with the red blood cells before addition of sPLA$_2$, which allows comparison of the inhibitory potency of annexin and modified annexins.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method for treating sickle-cell disease in a subject, comprising administering to said subject a pharmaceutical composition comprising a therapeutically effective amount of a modified annexin protein, wherein said modified annexin protein comprises a first annexin protein coupled to a second annexin protein, wherein the sickle-cell disease is treated.

2. The method of claim 1, wherein said first annexin protein is a first annexin V protein.

3. The method of claim 2, wherein said first annexin V protein comprises an amino acid sequence selected from the group consisting of:
   a) SEQ ID NO:3; and
   b) an amino acid sequence having at least 95% sequence identity to SEQ ID NO:3.

4. The method of claim 2, wherein said second annexin protein is a second annexin V protein.

5. The method of claim 4, wherein said second annexin V protein comprises an amino acid sequence selected from the group consisting of:
   a) SEQ ID NO:3; and
   b) an amino acid sequence having at least 95% sequence identity to SEQ ID NO:3.

6. The method of claim 4, wherein said modified annexin protein comprises an amino acid sequence selected from the group consisting of:
   a) SEQ ID NO:6; and
   b) an amino acid sequence having at least 95% sequence identity to SEQ ID NO:6.

7. The method of claim 1, wherein said first annexin protein is human annexin protein.

8. The method of claim 7, wherein said first annexin protein is coupled to said second annexin protein by a protein linker.

9. The method of claim 7, wherein said second annexin protein is human annexin protein.

10. The method of claim 9, wherein said first annexin protein is coupled to said second annexin protein by a protein linker.

11. A method for treating sickle-cell disease in a subject, comprising administering to said subject a pharmaceutical composition comprising a therapeutically effective amount of a modified annexin protein, wherein said modified annexin protein comprises an annexin V protein coupled to at least one a additional annexin V protein, wherein said isolated modified annexin protein comprises an amino acid sequence selected from the group consisting of:
  a) SEQ ID NO:6; and
  b) an amino acid sequence having at least 95% sequence identity to SEQ ID NO:6, wherein the sickle-cell disease is treated.

* * * * *

UNITED STATES PATENT AND TRADEMARK OFFICE
CERTIFICATE OF CORRECTION

PATENT NO. : 6,982,154 B2  Page 1 of 1
APPLICATION NO. : 10/632694
DATED : January 3, 2006
INVENTOR(S) : Anthony Allison It is certified that error appears in the above-identified patent and that said Letters Patent is hereby corrected as shown below:

Column 1, line 45, should be corrected to read -- infarction and consequent infection. Patients also suffer from --.

Column 6, line 11, should be corrected to read -- of sickle-cell disease. Splenic thrombosis often leads to --.

Column 7, line 1, should be corrected to read -- the inhibition of cellular amplification of platelet aggregation --; line 11 should be corrected to read -- and increased safety (PCT International Publication No. WO --.

Column 12, line 35, should be corrected to read -- annexin nucleic acid molecule. One embodiment is an iso- --.

Column 20, line 35, should be corrected to read -- ing vaso-occlusive crises, pain crises, Acute Chest Syndrome --.

Column 24, line 15, should be corrected to read -- annexin V binds to liposomes composed of 80% phosphati- --.

Signed and Sealed this

Eighteenth Day of December, 2007

JON W. DUDAS
*Director of the United States Patent and Trademark Office*